(12) United States Patent
Burch et al.

(10) Patent No.: US 7,771,426 B2
(45) Date of Patent: Aug. 10, 2010

(54) BONE TREATMENT INSTRUMENT AND METHOD

(75) Inventors: Shane Burch, San Francisco, CA (US); Brian C. Wilson, Toronto (CA); Stuart K. Bisland, Mississauga (CA)

(73) Assignee: University Health Network, Toronto (CA)

( * ) Notice: Subject to any disclaimer, the term of this patent is extended or adjusted under 35 U.S.C. 154(b) by 1399 days.

(21) Appl. No.: 10/969,910

(22) Filed: Oct. 22, 2004

(65) Prior Publication Data

US 2005/0143732 A1    Jun. 30, 2005

(51) Int. Cl.
   *A61B 17/56* (2006.01)
(52) U.S. Cl. .......................................... 606/53; 606/13
(58) Field of Classification Search .................. 606/1, 606/13, 15, 53; 607/88
   See application file for complete search history.

(56) References Cited

U.S. PATENT DOCUMENTS

| | | | |
|---|---|---|---|
| 4,681,103 A * | 7/1987 | Boner et al. ................... 606/1 |
| 5,127,407 A | 7/1992 | Tan | |
| 5,351,692 A * | 10/1994 | Dow et al. .................. 600/463 |
| 5,445,608 A * | 8/1995 | Chen et al. ................... 604/20 |
| 5,540,691 A * | 7/1996 | Elstrom et al. ............... 606/64 |
| 5,725,377 A | 3/1998 | Lemler et al. | |
| 5,942,534 A | 8/1999 | Trauner et al. | |
| 6,371,968 B1 * | 4/2002 | Kogasaka et al. ........... 606/190 |
| 6,602,274 B1 | 8/2003 | Chen | |
| 6,622,731 B2 | 9/2003 | Daniel et al. | |
| 7,359,601 B2 * | 4/2008 | Loeb .......................... 385/117 |
| 2002/0133148 A1 | 9/2002 | Daniel et al. | |
| 2002/0169453 A1 | 11/2002 | Berger | |
| 2003/0023243 A1 * | 1/2003 | Biedermann et al. .......... 606/73 |
| 2006/0041317 A1 * | 2/2006 | Hazebrouck et al. ....... 623/23.39 |
| 2006/0084944 A1 * | 4/2006 | Ferguson ........................ 606/1 |

FOREIGN PATENT DOCUMENTS

| | | |
|---|---|---|
| CA | 2423542 | 10/2003 |
| DE | 42 33 744 A1 | 4/1994 |
| EP | 0 812 574 A2 | 12/1997 |
| WO | WO 91/11966 | 8/1991 |
| WO | WO 01/00097 | 1/2001 |

OTHER PUBLICATIONS

Supplemental search report for corresponding European patent application EP04789764.0, dated Apr. 13, 2007.
Examination Report for corresponding European patent application No. 04 789 764.0, dated Apr. 8, 2008.
Examination Report for corresponding Canadian patent application No. 2,543,421, dated Mar. 18, 2008.

(Continued)

*Primary Examiner*—Ahmed M Farah

(57) ABSTRACT

Photodynamic therapy (PDT) is used in the case of bone. A photosensitizing drug is administered to a mammal. A bone insertion member is secured into bone. A fiber optic cable sheath extends from within the bone insertion member and is accessible. A fiber optic cable is inserted in the fiber optic cable sheath to deliver light to the bone. A locking member is then attached to the insertion member. Non-thermal light at a specific wavelength is then delivered to activate the drug. The insertion member and the fiber optic cable sheath may remain inside the mammal for further photodynamic therapy.

8 Claims, 22 Drawing Sheets

OTHER PUBLICATIONS

Tombolini, V., et al., Radiation therapy of spinal metastases: results with different fractionations. Tumori, 1994. 80(5): p. 353-6.

Walsh, G.L., et al., Anterior approaches to the thoracic spine in patients with cancer: indications and results. Ann Thorac Surg, 1997. 64(6): p. 1611-18.

Milker-Zabel, S., et al., Clinical results of retreatment of vertebral bone metastases by stereotactic conformal radiotherapy and intensity-modulated radiotherapy. Int J Radiat Oncol Biol Phys, 2003. 55(1): p. 162-7.

Katagiri, H., et al., Clinical results of nonsurgical treatment for spinal metastases. Int J Radiat Oncol Biol Phys, 1998. 42(5): p. 1127-32.

Ryu, S., et al., Image-guided and intensity modulated radiosurgery for patients with spinal metastasis. Cancer, 2003. 97(8): p. 2013-2018.

Fingar, V.H., et al., Analysis of acute vascular damage after photodynamic therapy using benzoporphyrin derivative (BPD). Br J Cancer, 1999. 79(11-12): p. 1702-8.

Takeuchi, Y., et al., Induction of intensive tumor suppression by antiangiogenic photodynamic therapy using polycation-modified liposomal photosensitizer. Cancer, 2003. 97(8): p. 2027-34.

Rousset, N., et al., Cellular distribution and phototoxicity of Benzoporphyrin derivative and Photofrin. Res Exp Med (Berl), 2000. 199(6): p. 341-57.

Wiedmann, M., et al., Neoadjuvant photodynamic therapy as a new approach to treating hilar cholangiocarcinoma: a phase II pilot study. Cancer, 2003. 97(11): p. 2783-90.

Sutedja, G. And P.E. Postmus, The role of photodynamic therapy in the management of stage I/11 NSCLC. Lung Cancer, 2001.34 Suppl 3: p. S35-S38.

Hendren, S.K., et al., Phase II trial of debulking surgery and photodynamic therapy for disseminated intraperitoneal tumors. Ann Surg Oncol, 2001. 8(1): p. 65-71.

Nathan, T.R., et al., Photodynamic therapy for prostate cancer recurrence after radiotherapy: a phase I study. J Urol, 2002. 168(4 Pt 1): p. 1427-32.

Engebraaten, O. and O. Fodstad, Site-specific experimental metastasis patterns of two human breast cancer cell lines in nude rats. Int J Cancer, 1999. 82(2): p. 219-25.

Weber, K.L. and M.C. Gebhardt, What's new in musculoskeletal oncology. J Bone Joint Surg Am, 2003. 85 A(4): p. 761-7.

Faul, C.M. and J.C. Flickinger, The use of radiation in the management of spinal metastases. J Neurooncol, 1995. 23(2): p. 149-61.

Wedin, R., H.C. Bauer, and L.E. Rutqvist, Surgical treatment for skeletal breast cancer metastases: a population-based study of 641 patients. Cancer, 2001. 92(2): p. 257-62.

Sundaresan, N., et al., Treatment of neoplastic spinal cord compression: results of a prospective study. Neurosurgery, 1991. 29(5): p. 645-50.

Rousset, N., et al., Effects of photodynamic therapy on adhesion molecules and metastasis. J Photochem Photobiol B, 1999. 52(1-3): p. 65-73.

Richter, A.M., et al., Photosensitising efficiency of two regioisomers of the benzoporphyrin derivative monoacid ring A (BPD-MA). Biochem Pharmacol, 1992. 43(11): p. 2349-58.

Richter, A.M., et al., Photosensitizing potency of structural analogues of benzoporphyrin derivative (BPD) in a mouse tumour model. Br J Cancer, 1991. 63(1): p. 87-93.

Jamieson, C.H., W.N. McDonald, and J.G. Levy, Preferential uptake of benzoporphyrin derivative by leukemic versus normal cells. Leuk Res, 1990. 14(3): p. 209-19.

Richter, A.M., et al., Biodistribution of tritiated benzoporphyrin derivative ($^3$H-BPD-MA), a new potent photosensitizer, in normal and tumor-bearing mice. J Photochem Photobiol B, 1990. 5(2): p. 231-44.

Gluck, S., et al., The selective uptake of benzoporphyrin derivative mono-acid ring A results in differential cell kill of multiple myeloma cells in vitro. Photochem Photobiol, 1996, 63(6): p. 846-53.

Kurohane, K., et al., Photodynamic therapy targeted to tumor-induced angiogenic vessels. Cancer Lett, 2001. 167(1): p. 49-56.

Momma, T., et al., Photodynamic therapy of orthotopic prostate cancer with benzoporphyrin derivative: local control and distant metastasis. Cancer Res, 1998. 58(23): p. 5425-31.

Cincotta, L. et al., Benzophenothiazine and benzoporphyrin derivative combination phototherapy effectively eradicates large murine sarcomas. Photochem Photobiol, 1996. 63(2): p. 229-37.

Richter, A.M., et al., Liposomal delivery of a photosensitizer, benzoporphyrin derivative monoacid ring A (BPD), to tumor tissue in a mouse tumor model. Photochem Photobiol, 1993. 57(6): p. 1000-6.

Takeuchi, A., et al., A new method of bone tissue measurement based upon light scattering. J Bone Miner Res, 1997. 12(2): p. 261-6.

Casas, A., et al., In vitro photosensitisation of a murine mammary adenocarcinoma cell line with Verteporfin. Cell Mol Biol (Noisy-le-grand), 2002.48(8): p. 931-7.

Rehemtulla, A., et al., Rapid and quantitative assessment of cancer treatment response using in vivo bioluminescence imaging. Neoplasia, 2000. 2(6): p. 491-5.

Wetterwald, A., et al., Optical imaging of cancer metastasis to bone marrow: a mouse model of minimal residual disease. Am J Pathol, 2002. 160(3): p. 1143-53.

Koudinova, N. et al., Photodynamic Therapy with Pd-Bacteriopheophorbide (TOOKAD): Successful In Vivo Treatment of Human Prostatic Small Cell Carcinoma Xenografts. Int. J. Cancer, 2003. 104, p. 782-789.

Kusuzaki, K. et al., Total Tumor Cell Elimination with Minimum Damage to Normal Tissues in Musculoskeletal Sarcomas following Photodynamic Therapy with Acridine Orange. Oncology 2000. 59. p. 174-180.

Meyer, M. et al. The study of the effects of photodynamic therapy on the normal tissues of the rabbit jaw, Br J. Cancer 1991, 64(6), p. 1093-1097.

Fan, K. et al., Photodynamic Therapy on Normal Rabbit Mandible, Proc. SPIE vol. 2371, 5th International Photodynamic Association Biennial Meeting: Denis A. Cortese; Ed., 1995, p. 449-450.

web pages from www.burtonreport.com/InfSpine/SurgStabilPedScrews.htm "Pedicle Screw Segmental Instrumentation", printed Oct. 19, 2004 (6 pages).

web pages from www.spine-health.com/topics/surg/overview/lumbar/lumb09_ped.html "Pedicle screws for spine fusion", by Peter F. Ullrich, Jr., MD, Sep. 8, 1999 (Updated Jan. 20, 2004) printed Oct. 19, 2004 (6 pages).

Kriska et al. Role of mitochondrial cardiolipin peroxidation in apoptotic photokilling of 5-aminolevulinate-treated tumor cells, Archives of Biochemistry and Biophysics 433 (2005) p. 435-446.

Exam Report for corresponding European patent application EP04789764.0, dated Nov. 21, 2007.

* cited by examiner

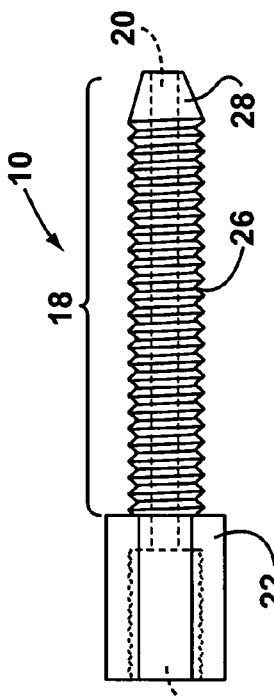
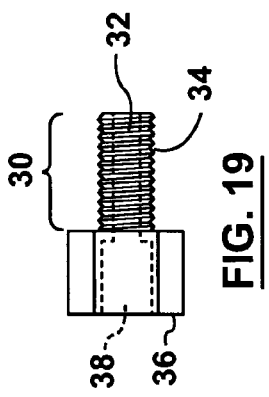
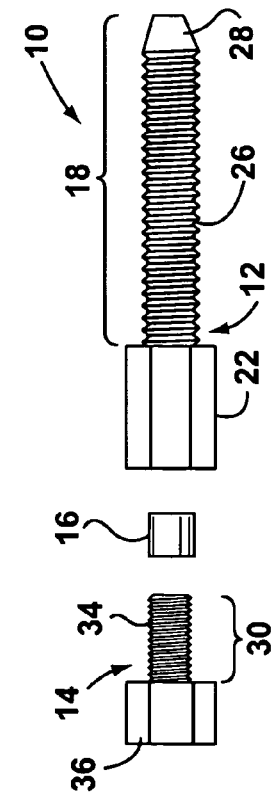
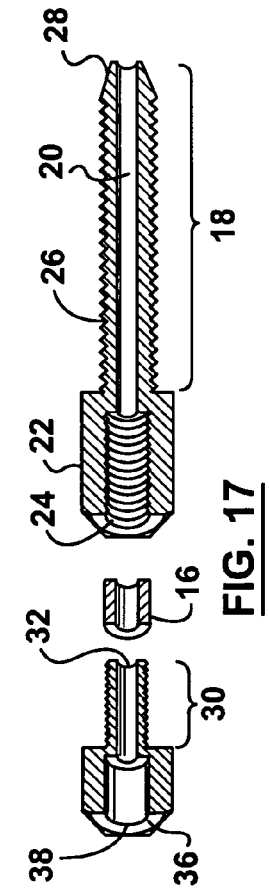
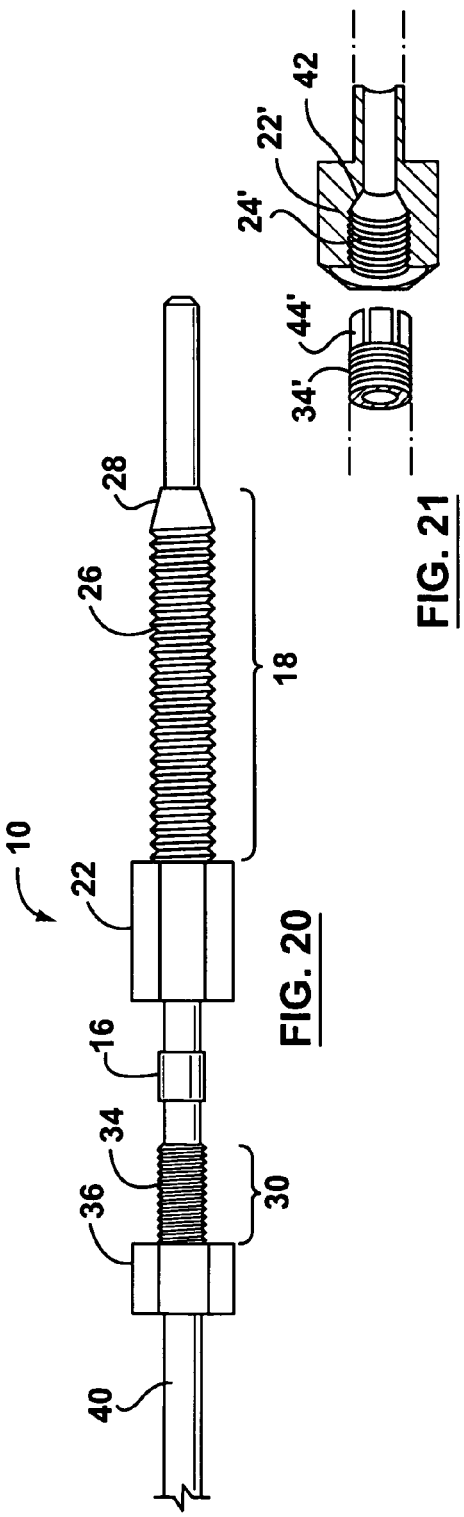
FIG. 16
FIG. 17
FIG. 18
FIG. 19
FIG. 20
FIG. 21

BONE TREATMENT INSTRUMENT AND METHOD

REFERENCE TO RELATED APPLICATION

This application claims priority from Canadian Patent Application Serial No. 2,446,663 filed on Oct. 24, 2003.

FIELD OF THE INVENTION

This invention relates generally to treatment of bone, bone tumors and lesions, and diseases of the bone.

BACKGROUND OF THE INVENTION

Approximately 1.3 million cases of cancer were diagnosed in North America in 2001. Over 50% of these have the potential to metastasize to bone [14]. Each year, over one hundred thousand bone metastases are identified. Post-mortem autopsy results from patients with primary cancer indicate that 60% of spines examined had metastatic lesions. An estimated twenty to forty thousand cases of metastatic breast cancer lesions alone occur in the spine each year [1,2]. Metastatic lesions to the spine result in intractable back pain, loss of bowel and bladder function, paresis and paralysis. The lesions can affect singular or multiple vertebral bodies.

In the ambulatory patient the mainstay of treatment is radiation therapy, while surgery is reserved for those experiencing collapse or neurological compromise. Unfortunately radiation therapy provides only limited relief from pain, does not provide stability to the spine and adversely affects the soft tissue such that the morbidity and mortality of surgical intervention is increased threefold [3,4,5]. Results of radiation therapy for the treatment of spinal metastases have shown that only one third have complete relief of their back pain [15]. Radiation therapy is limited by the number of times it can be administered as it affects the integrity of the soft tissues and can induce radiation myelopathy. As the longevity of patients with spinal metastases increases (average survival 2 years with breast cancer, mean 1 year survival of 78%) [16] so does the likelihood of lesion recurrence and the necessity for spinal surgery. Recurrence with radiation therapy is estimated to be 33% [1,17]. Spinal surgery for patients with spinal metastases carries a 30-40% risk of morbidity and a 7-16% risk of mortality.

Photodynamic therapy (PDT) can directly target lesions. PDT ablates tissue with a non-thermal specific wavelength of light delivered to the targeted tissue. A photosensitizing compound is administered prior to the light. The light activates the compound to a chemically excited state, the energy of which is then transferred to molecular oxygen producing reactive oxygen-derived species that are toxic to the surrounding tissue [8,18] [19,20]. There are reports that the drug is preferentially taken up and retained in tumor tissue compared to normal tissue [21,22] making the treatment somewhat specific. This therapy has been used in lung [9,10], intraperitoneal [11] and prostate cancer [12].

There are several photosensitizing compounds now available with minimal systemic side effect profiles. Benzoporphyrin derivative monoacid ring A (BPD-MA) is a photosensitizer that can be used to either target the neo-vasculature or produce intracellular cytotoxic effects based on the drug-light interval [6,7,23,24,25,26]. The vascular targets are primarily affected if the drug light interval is short (15 minutes or less) while the intracellular effects are seen in tissue if the drug light interval is long (3 hours) [6,24]. There are several reports of its use in soft tissue tumors in the murine model [20,23,25, 27] as well as of its use in an orthotopic chondrosarcoma [6] and fibrosarcoma tumor models [24,26]. Results from these studies showed a significant effect at both the 15 minute and 3 hour drug light interval was achieved with 33% of the lesions being completely ablated at 4 weeks post treatment. The greatest effect was seen with the shorter interval demonstrating the potency of BPD-MA to affect the neo-vasculature.

To date, there have not been any published reports of the use of this therapy in bone or in the spine. To date, there have not been any published reports of PDT use in an in vivo metastatic breast cancer model affecting bone. To date, there have not been any published reports of the pharmacokinetics of BPD-MA for bone. There is a paucity of literature on the optical properties of bone.

Takeuchi et al., 1997 [28], reported on the optical properties of cancellous and cortical bone in comparison to muscle, fat and saline. Cortical bone has a high attenuation to light while cancellous bone does not.

SUMMARY OF THE INVENTION

In a first aspect, at least one embodiment of the invention provides a device for enabling light-based therapy for a treatment area of a mammal. The device comprises an insertion member including a first shaft having a first bore through at least a portion thereof with a first diameter sized for receiving a light conduit; and, a first head portion near the proximal end of the first shaft having a second bore extending therethrough, the second bore having a second diameter larger than the first diameter. The device also includes a locking member releasably connectable to the insertion member, the locking member including a second shaft having a third bore therethrough with a third diameter, the third diameter being less than the second diameter but being sized for receiving the light conduit; and, a gripping means disposed within the second bore of the insertion member for holding the conduit in place when the locking member is connected to the insertion member.

In another aspect, at least one embodiment of the invention includes a use of a device with an optical conduit, the device adapted for fixing the optical conduit in bone during the delivery of photodynamic therapy in bone.

In yet another aspect, at least one embodiment of the invention provides a method for treating a treatment area of a mammal via photodynamic therapy comprising:

a) inserting an insertion member near the treatment area, the insertion member having an internal bore along at least a portion thereof for receiving and guiding an optical conduit to the treatment area;

b) inserting the optical conduit into the insertion member;

c) securing a locking member to the insertion member for holding the optical conduit in place; and, d) providing light energy via the optical conduit to treat the treatment area.

In another aspect, at least one embodiment of the invention includes a device for providing light-based therapy for a treatment area of a mammal. The device comprises a light conduit for delivering the light-based therapy; an insertion member for inserting at or near the treatment area, the insertion member having a bore sized for receiving the light conduit; and, a locking member releasably connectable to the insertion member for holding the light conduit in place during treatment.

BRIEF DESCRIPTION OF THE DRAWINGS

For a better understanding of the present invention, and to show more clearly how it may be carried into effect, reference will now be made, by way of example, to the accompanying drawings which show some embodiments of the present invention, and in which:

FIG. 16 shows a side view of a disassembled device for use with providing light-based therapy in accordance with the invention;

FIG. 17 shows a side cross-section view of the components of the disassembled device of FIG. 16;

FIG. 18 shows a cross-sectional view of an insertion member of the device;

FIG. 19 shows a cross-sectional view of a locking member of the device;

FIG. 20 shows an isometric view of the components of the device being assembled with an optical conduit;

FIG. 21 shows an alternative embodiment of the insertion and locking members of the device;

DETAILED DESCRIPTION OF EMBODIMENTS OF THE INVENTION

Figure 1:
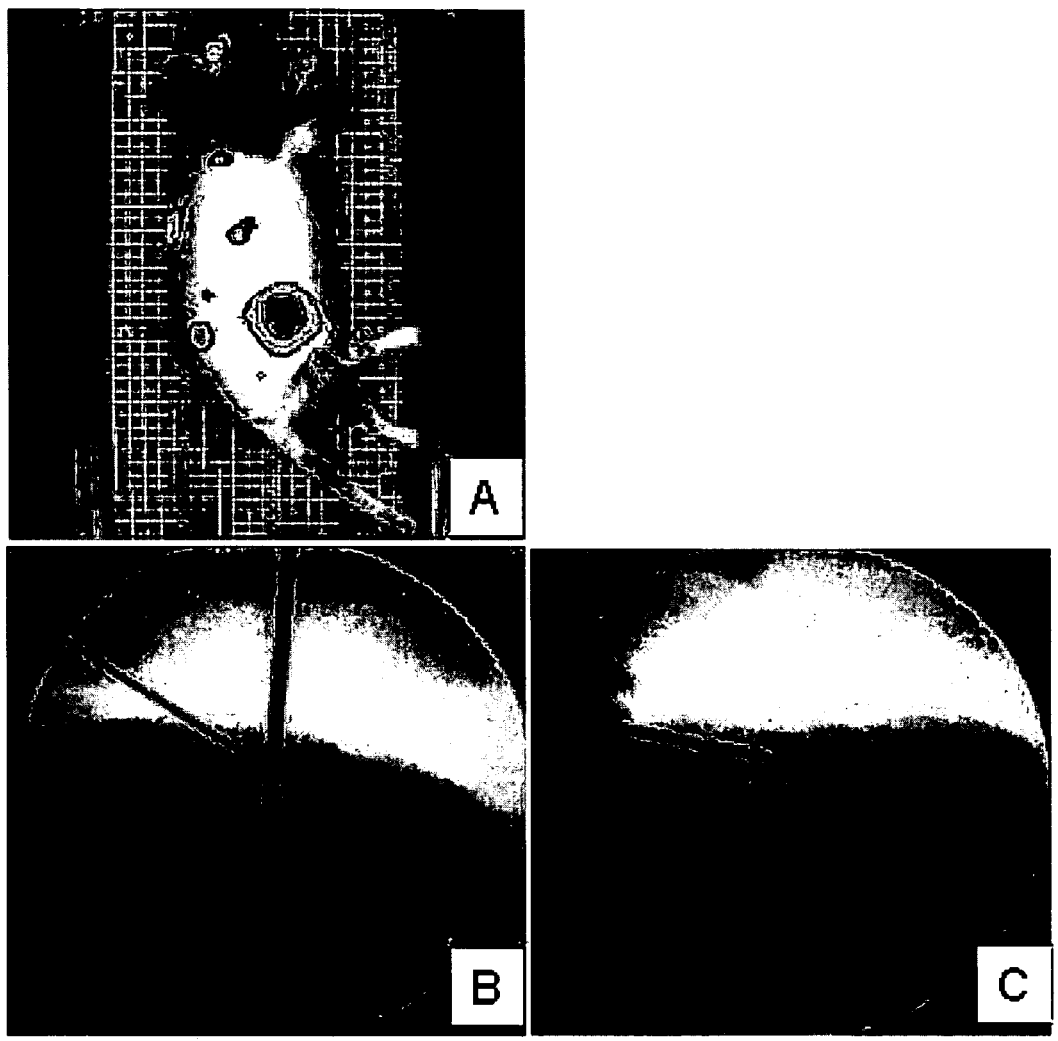
FIG. 1 shows stereotactic targeting of bioluminescent metastatic lesions in a rat using a mini-C-arm image intensifier.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements. In addition, numerous specific details are set forth in order to provide a thorough understanding of the invention. However, it will be understood by those of ordinary skill in the art that the invention may be practiced without these specific details. In other instances, well-known methods, procedures and components have not been described in detail so as not to obscure the invention.

In some embodiments of the invention, photodynamic therapy (PDT) is used in bone. The method involves administering a photosensitizing drug to a mammal having bone tumors or other bone disease. A "bone tumor" refers to a primary or metastatic tumor associated with bone, that is, a tumor on or in a bone. A non-exhaustive list of photosensitizing drugs includes benzoporphyrin derivative monoacid ring A (BPD-MA) (also known as verteporfin and Visudyne®), palladium-bacteriopheophorbide (known as TOOKAD®), and 5-aminolaevulinic acid (ALA). Non-thermal light of a specific wavelength suitable for stimulating the photosensitizing drug is applied to the drug within the bone. The photosensitizing drug may target the neo-vasculature and/or produce intracellular cytotoxic effects and/or inhibit growth of or destroy the tumor cells in some other manner.

For small bones a fiber optic cable is inserted into the mammal and placed adjacent a bone lesion. For larger bones such as, for example, pig and human vertebrae, a cannulated bone screw is secured into the bone. The cannulated bone screw has a head, an externally-threaded shaft and a frustroconical tip. A fiber optic cable sheath is located inside the cannula of the screw and extends from the tip of the bone screw beyond the screw to at least the skin of the mammal. Photodynamic therapy can be used on one or more occasion by administering a photosensitizing drug, inserting a fiber optic cable into the fiber optic cable sheath, and delivering the light through the fiber optic cable. The bone screw and the fiber optic cable sheath remain in place from one PDT treatment to the next. Once it has been decided not to use PDT treatment at the site of the bone screw anymore, the fiber optic cable sheath is removed and bone cement is injected into the bone screw.

The results of in vitro studies indicated that cells from a human metastatic breast cancer cell line (MT-1) were susceptible to PDT with BPD-MA while the cells were not sensitive to the drug or the light individually. This is consistent with reports in the literature [23,29]. Furthermore, uptake into MT-1 cells was demonstrated directly with real time fluorescent microscopy indicating that these cells were susceptible to intracellular cytotoxic effects of PDT.

In vivo studies in a rat model demonstrated the effectiveness of PDT on bone tumors from a human metastatic breast cancer cell line. A bioluminescent metastatic model in the nude rat was developed to facilitate the localization and targeting of the lesions.

As part of these studies, the drug uptake studies indicated that the spinal cord had minimal uptake of BPD-MA suggesting that it would not be susceptible to damage during treatment. The fluorescence microscopy however, indicated that BPD-MA is taken up into the spinal cord. Furthermore it showed that the drug has a delayed uptake (greater than 1 hour) and suggested that the optimal drug light interval prior to PDT would be less than 1 hour or greater than 24 hours.

The model used in this study was a purely metastatic model involving a human breast cancer cell line. Engebraaten and Fodstad, 1999, demonstrated lesions within all vertebrae and of mu/mu rats between 14 and 21 days [13]. In this study metastases occurred in the spine, long bones and lung. Fine detail radiography revealed lesions within long bones as early as 14 days post tumor injection. Rapid weight loss was seen after 18 days post injection followed by overt tumors in the mandible and distal femur and proximal tibia. Paralysis and death secondary to tumor burden occurred typically around day 21 and 23 respectively. Micro-CT scanning revealed multiple large lytic lesions within most vertebrae and long bones of affected animals. Subsequent histological analysis confirmed the presence of the tumor within the vertebrae and long bones and demonstrated the invasiveness of the tumor. The bioluminescence allowed determination of the growth of the lesions, location of the tumor and a way of targeting the tumor. In addition, bioluminescence has been shown to be quantitative in determining tumor ablation in vitro as well as in vivo [30,31]. Furthermore by imaging the tumor with bioluminescence, growth of the tumor could be assessed, lesions could be detected early, then targeted and early treatment could be administered.

The in vivo results demonstrate the effectiveness of this therapy in treating a human metastatic breast cancer in both the vertebrae and long bones. The results indicate that PDT can ablate tumor tissue within bone and that the in vivo structure of bone and bone marrow is not a limiting factor for this therapy. The bioluminescent data indicated that a 99.8% reduction in tumor growth was obtained with one treatment. The largest area of effect had a diameter of 2.2 cm and was created by a 200 um fiber optical cable with a treatment time of 16 minutes. The results also indicate that the area of tumor ablated is directly proportional to the amount of light supplied to the targeted area. A shorter treatment time (3 minutes) produced a smaller effect than longer treatment times with a 66% reduction in the tumor growth with the 25 J group. Based on work by Richter et al., [22] in the mouse, the inventor hypothesized that 24 hour drug-light interval would be selective for tumor ablation. Yet, this was not the case. There was no difference between control animals and those animals treated with a 24 hour drug light interval with respect to ablation of tumor tissue.

The spinal cord in the rat is very sensitive to PDT as the drug is taken up into the cord by 3 hours. We anticipated that a window of opportunity would exist based on the delay of transport of the drug across the drug-spinal cord barrier, yet, even at short drug-light intervals when drug was not seen in the spinal cord by fluorescence microscopy paralysis was seen. This indicates that in the rat model the effect was vascular in nature while the spinal cord is also susceptible to cytotoxic damage as drug light intervals of 3 hours had an effect. Note that treatment with light only or drug only did not affect the tumor, bone, bone marrow or spinal cord. The nerve roots and peripheral nerves were not affected following treatment at the 3 hour drug light interval at any light dose. No paralysis was seen when treatment was administered with a 24 hour drug light interval.

In summary the results suggest that PDT with BPD-MA could be an effective treatment directed against metastatic tumors in bone. This treatment would be used preferentially to treat tumors within the vertebrae through a trans or parapedicular approach and implemented to treat multiple vertebrae. The size of the lesions produced in the rat spine defined an area of effect that is well suited for lesions within human vertebrae. The area of effect can be varied easily allowing for safe operating parameters around the spinal cord. However, in larger vertebrae in which the fiber optic cable is implanted within the bone the inventor anticipates the effect on the spinal cord will be negligible. Studies in larger animals are required to establish the safety of this treatment in the spine.

Figure 13:
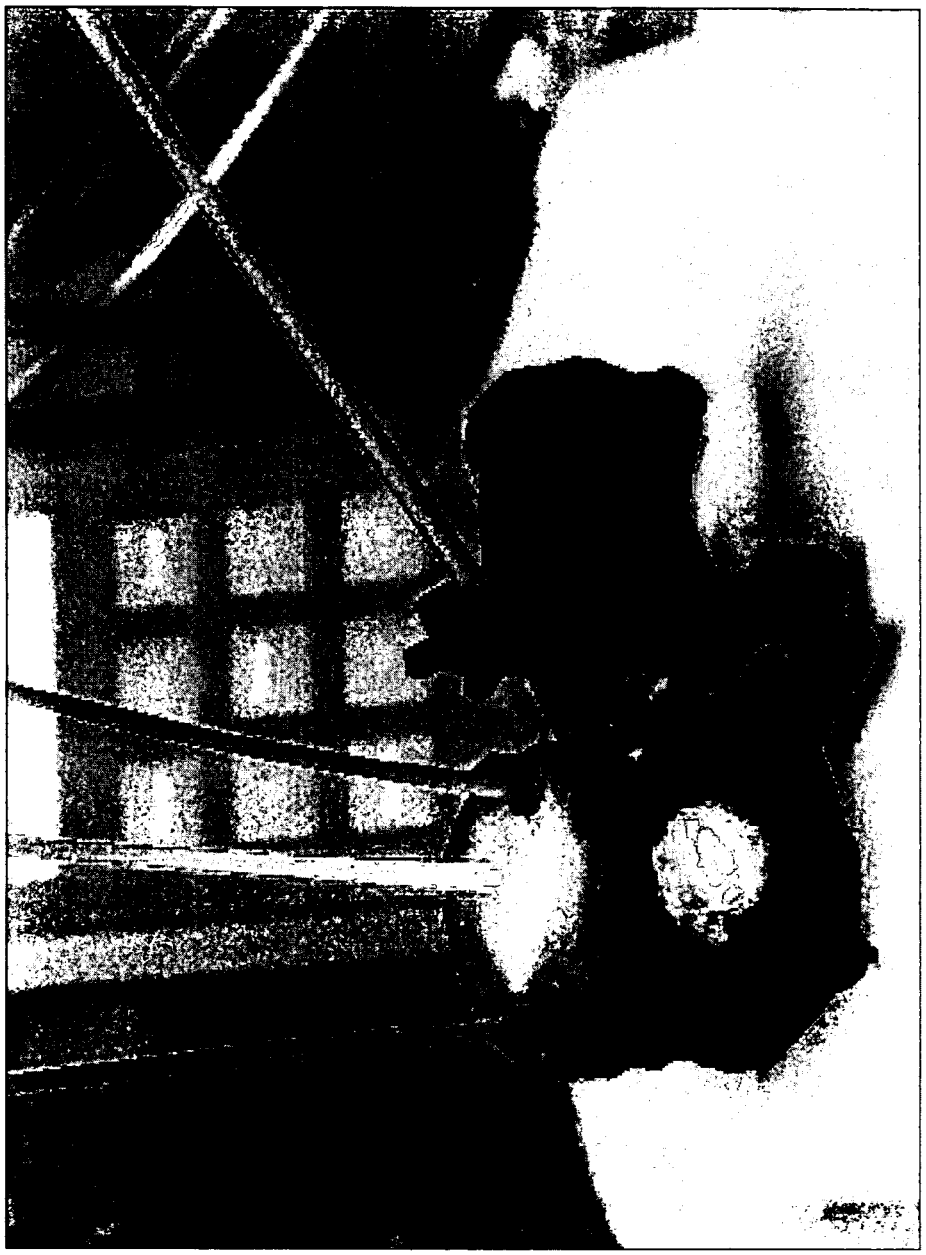
FIG. 13 is a photograph of light passing through a human cadaver vertebrae.

Studies of light attenuation in human cadaver vertebrae demonstrated the feasibility of PDT in large bones. FIG. 13 is a photograph from these studies.

In vivo studies in a pig model demonstrated the feasibility of a procedure using a cannulated bone screw to stabilize a large bone and to facilitate delivery of light to the bone. The in vivo studies in the pig model also measured the attenuation of light within a vertebral body, and from the derived data, safe doses of light and drug were determined.

These studies, as well as a detailed description of the surgical procedure using the cannulated bone screw, will now be described in more detail.

In Vitro Studies

In Vitro Uptake of BPD-MA in MT-Cells:

Method: MT-1 cells, a human breast cancer cell line, provided courtesy of Dr. O. Engebraaten, Norwegian Radium Hospital, Oslo, Norway, were grown and maintained in RPMI media containing penicillin and streptomycin with 10% fetal bovine serum at 37 degrees Celsius. Once the cells had reached subconfluence they were resuspended in free RPMI. The cells were harvested using a 0.05% trypsin—0.05 mM EDTA solution. Cells were then counted with a hemocytometer and plated at $2 \times 10^5$ cells/ml in an inverted microscopy slide chamber in PBS. BPD-MA was then added to the suspension at a concentration of 1 ug/ml. The cells were then visualized under bright field and fluorescence microscopy (Zeiss Axiophot) using an excitation/emission filter of 490 nm/emission respectively. Uptake of drug into the cells was monitored overtime using live video photography with a CCD camera attached to the microscope.

Figure 2:
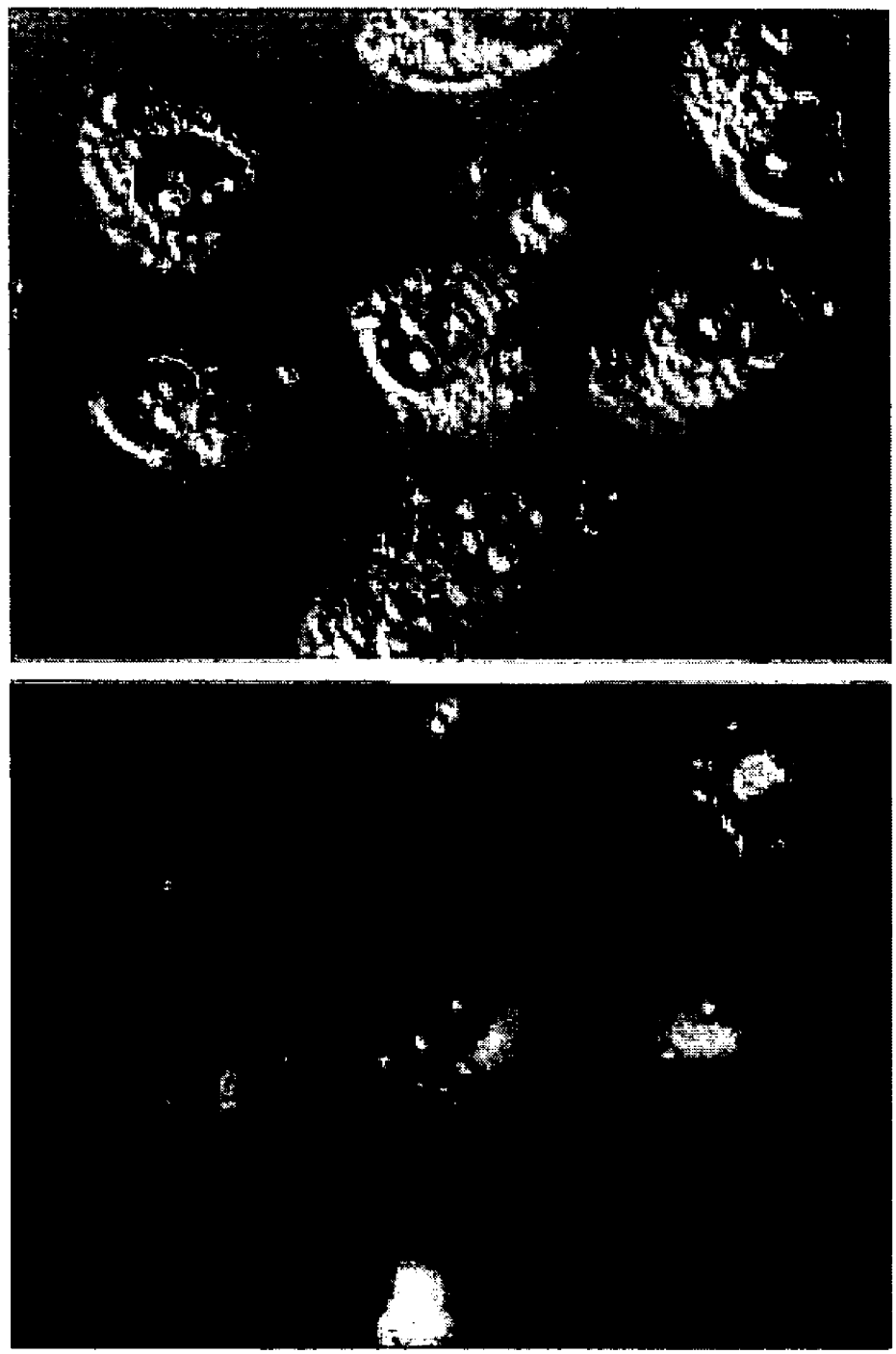
FIG. 2 shows the in vitro uptake of BPD-MA in MT-1 cells.

Results: FIG. 2 shows the in vitro uptake of BPD-MA in MT-1 cells. A) is a bright field microscopy image of MT-1 cell (63×) and C) is an overlay of the bright field and fluorescent image showing colocalization of BPD-MA within MT-1 cells (63×). The MT-1 cells began fluorescing at 45 minutes following incubation with BPD.

PDT Effect on In Vitro MT-1 Cells:

Method: MT-1 cells were grown and maintained in RPMI media containing penicillin and streptomycin with 10% fetal bovine serum at 37 degrees Celsius. Once the cells had reached subconfluence they were resuspended in free RPMI. The cells were harvested using 0.05% trypsin—0.05 mM EDTA solution. Cells were then counted with a hemocytometer and plated at $2 \times 10^5$ cells/ml in a 96 well plate. BPD-MA was then added to the individual wells at a concentration of 1 ug/ml or 10 ug/ml. A 690 nm light was administered at 150 mW to the individual wells at a fluence of either 100 $J/cm^2$ or 25 $J/cm^2$ following an 8 hour incubation period. Control wells included those that did not contain cells, those that contained cells but no BPD-MA, those that contained cells and drug but did not receive a light does and those that contained cells and received a light dose but were not incubated with BPD-MA. Following treatment the cells were allowed to survive for 24 hours following which an SRB assay was performed to establish the number of viable cells remaining. Briefly, cells were fixed in 10% trichloroacetic acid and stained with a sulpharodamine bromide solution selectively staining viable cells. A spectrophotometer was then used to assess the absorbance of 540 nm light within individual wells of the 96 well plate which was correlated to the number of remaining cells following treatment.

Figure 5:
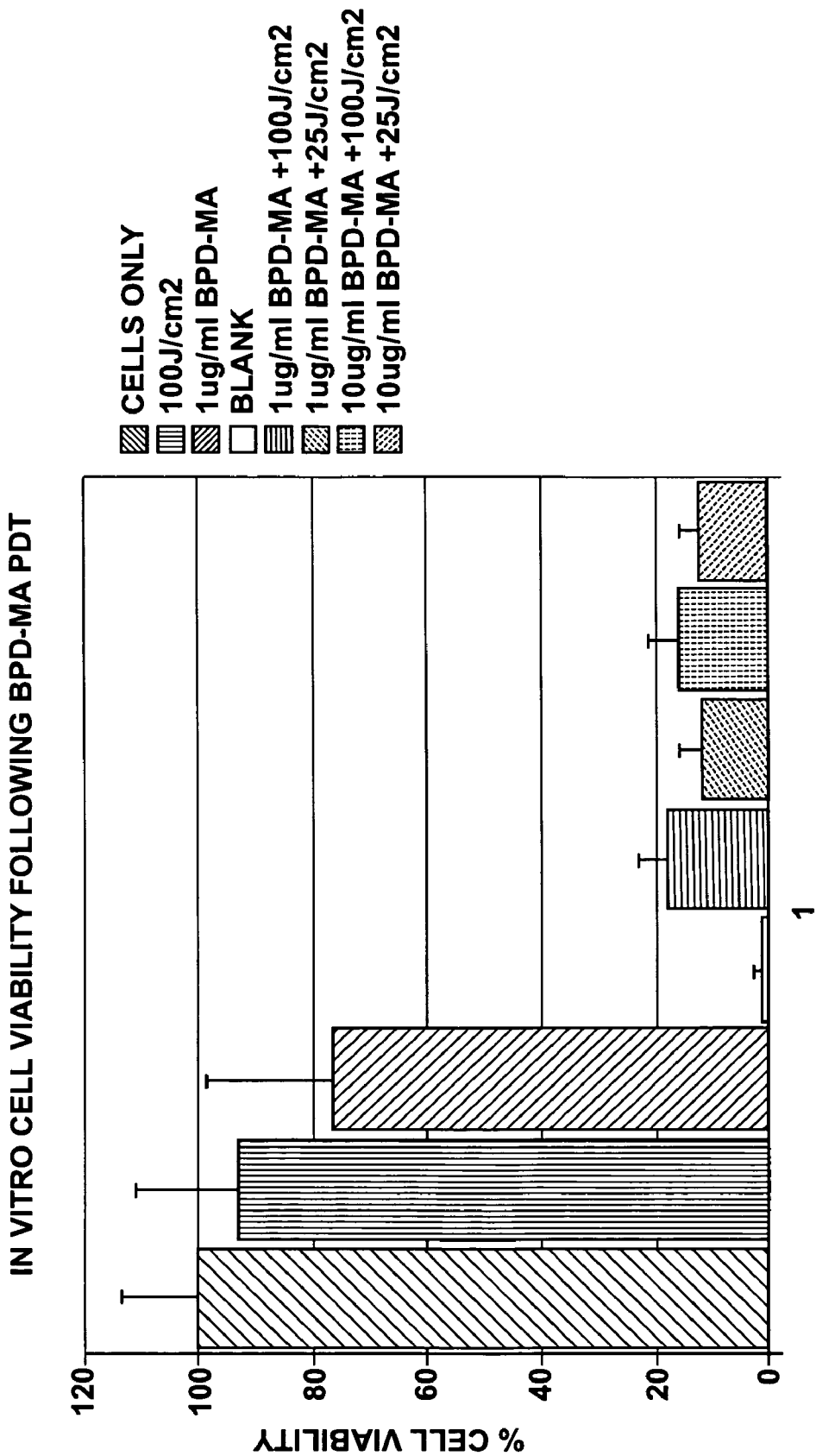
FIG. 5 is a bar graph of the in vitro cell viability following BPD-MA PDT.

Results: The effect of PDT on in vitro MT-1 cells was demonstrated using an SRB assay. A significant difference was seen between the absorbance in the untreated wells versus the wells treated with light and drug. No significant difference was seen between untreated wells and wells treated with light only or drug only (Table 1). As shown in FIG. 5, there was no difference between the two drug concentrations (10 ug/ml and 1 ug/ml BPD-MA) with respect to the treatment group and there was no significant difference in absorbance between BPD-MA wells treated with either 100 J/cm$^2$ or 25 J/cm$^2$.

TABLE 1a

SRB Assay

| Group | Drug Dose | Light Dose | Standard Mean (absorbance) | Standard Deviation | 95% Confidence Interval |
|---|---|---|---|---|---|
| 1 | 1 ug/ml x | 200 J/cm$^2$ | .2923 | .0794 | .2419 |
| 2 | 1 ug/ml x | 25 J/cm$^2$ | .1946 | .0618 | .1553 |
| 3 | 10 ug/ml x | 200 J/cm$^2$ | .2558 | .0865 | .2009 |
| 4 | 10 ug/ml x | 25 J/cm$^2$ | .2049 | .0523 | .1717 |
| 5 | No cells | No cells | .0206 | .0269 | .0035 |
| 6 |  | 200 J/cm$^2$ | 1.4954 | .2884 | 1.3122 |
| 7 | 1 ug/ml | / | 1.2392 | .3417 | .8806 |
| 8 | Cells Only | Cells Only | 1.5992 | .2800 | 1.4212 |

/ indicates absence of variable

TABLE 1b

SRB Assay ANOVA with Bonferroni for multiple comparisons (* indicate significant difference between groups)

| Group | Mean | 5 | 2 | 4 | 3 | 1 | 7 | 6 | 8 |
|---|---|---|---|---|---|---|---|---|---|
| 5 | .0206 |   |   |   |   |   |   |   |   |
| 2 | .1946 |   |   |   |   |   |   |   |   |
| 4 | .2049 |   |   |   |   |   |   |   |   |
| 3 | .2558 | * |   |   |   |   |   |   |   |
| 1 | .2923 | * |   |   |   |   |   |   |   |
| 7 | 1.2392 | * | * | * | * | * |   |   |   |
| 6 | 1.4954 | * | * | * | * | * |   |   |   |
| 8 | 1.5992 | * | * | * | * | * | * |   |   |

In Vivo Studies in Rat Model

BPD Uptake in the Serum and Spinal Cord

Method: BPD-MA was administered to 10 rats (Sprague-Dawley, 150 gm) through a tail vein injection. Animals were then sacrificed using $CO_2$ inhalation overdose at 16 minutes, 3 hrs, 6 hrs and 24 hrs following injection. Control animals without BPD-MA were euthanized in a similar fashion. Serum samples and spinal cord tissue samples were harvested from the animals at the time of euthanasia. A segment of spine was also fixed in 10% formalin for 7 days followed by decalcification for 7 days in 10% formic acid for fluoroscopic microscopic analysis. A control assay determined that BPD-MA fluorescence was not affected by formic acid. BPD-MA concentration within the serum and spinal cord tissue was then determined using fluorimetry. Briefly, the samples were solubilized and the samples were tested with excitation and emission spectra specific to BPD-MA. The fluorescence of the drug within the tissue was correlated to the specific uptake of the drug within the tissue. Fluorescent microscopy was also used to visualize the presence or absence of BPD-MA within the vertebrae and spinal cord at 1 hour, 3 hours and 24 hours.

Figure 3:
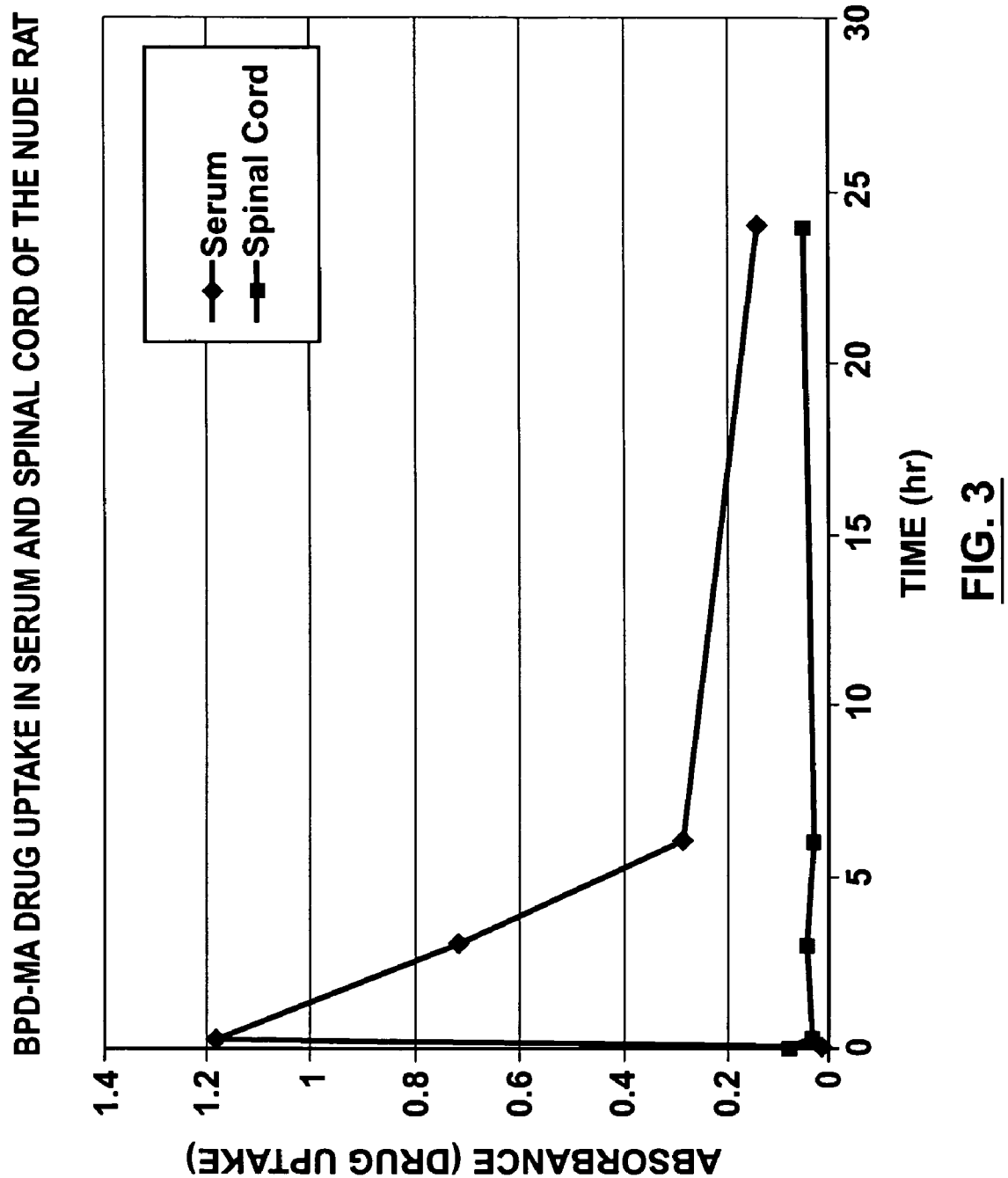
FIG. 3 is a plot of the BPD-MA drug uptake in serum and spinal cord of the nude rat.
Figure 4:
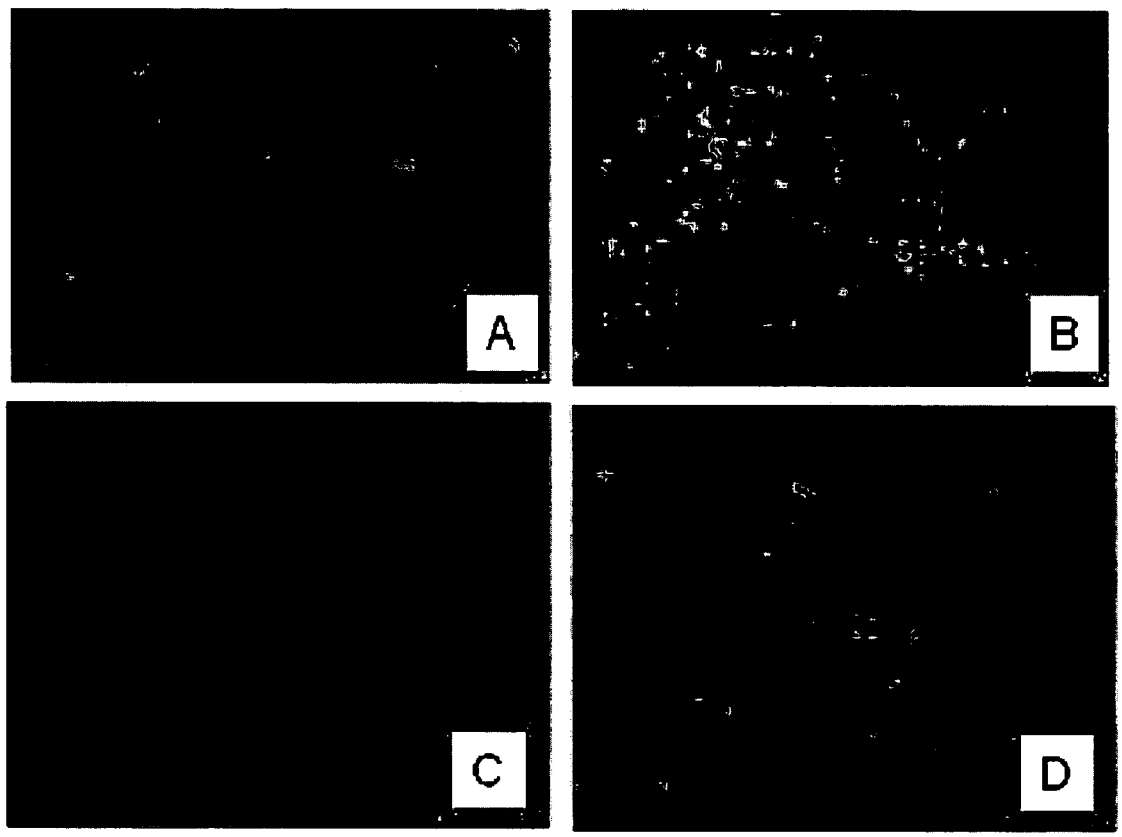
FIG. 4 shows fluorescence microscopy of BPD-MA uptake in the spinal cord and vertebrae of the nude rat.

Results: Fluorimetry was used to determine the specific uptake of the BPD in the spinal cord at 15 minutes, 3 and 24 hours post injection. As shown in FIG. 3, the specific uptake studies indicated that there was rapid increase in the serum drug concentration over 15 minutes but began to decline after 3 hours and returned to baseline by 24 hours post injection. BPD-MA fluorescence was evident within the spinal cord at 3 hours post administration. FIGS. 4A-D show fluorescence microscopy of BPD-MA uptake in the spinal cord and vertebrae. FIG. 4A shows the uptake of BPD-MA in the vertebrae at 15 minutes, FIG. 4B shows the uptake of PD-MA in the vertebrae at 3 hours, FIG. 4C shows the uptake of BPD-MA in the spinal cord at 15 minutes, and FIG. 4D shows the uptake of BPD-MA in the spinal cord at 3 hours. Sagittal and coronal sections from the Sprague-Dawley rat vertebrae examined under fluorescent microscopy indicated that there was delayed uptake into the spinal cord with no drug being present at 1 hour, yet, at 1 hour the bone marrow contained signal. At 3 hours the spinal cord and bone marrow contained an intense signal with neuronal cell bodies being labeled within the cord. At 24 hours the fluorescence of the drug within the spinal cord and vertebrae returned to baseline levels.

Spinal Metastases Model:

Method: Ten nude mu/mu (Harlan) female rats (4-6 weeks of age) were used in this part of the study. The animals were injected with MT-1 cells, a human breast cancer cell line, provided courtesy of Dr. O. Engebraaten, Norwegian Radium Hospital (Oslo, Norway) who had previously shown [13] that injection of these cells into the left ventricle in 4 week old nude rats produced spinal and boney metastases in all animals injected. The cells were grown and maintained in RPMI media containing penicillin and streptomycin with 10% fetal bovine serum at 37 degrees Celsius. The protocol was in accordance with standards of the Canadian Council on Animal Care. The chest of each animal was then prepared with alcohol and $2\times10^6$ cells of MT-1 were injected into the left ventricle using a 1 ml syringe with a 26 g needle. Pulsatile blood in the syringe was ensured prior to each injection. The animals were placed back into their cages and fed water and rat chow ad libitum and kept on a constant light dark cycle. The animals were then imaged by fine detail radiography at 14 and 21 days post injection. The animals were examined for overt tumors, paralysis and cachexia following injection. The animals were sacrificed using $CO_2$ inhalation for compassionate reasons between day 23 and day 30 depending on individual tumor burden. Vertebrae and long bones were then harvested and fixed in 10% formalin for 7 days. Micro-CT images were obtained and then the samples were decalcified in 10% formic acid for 7 days. The tissue was then blocked, paraffin embedded and analyzed under light microscopy using H&E staining.

Establishment of a Transfected Human Breast Cancer Cell Line Expressing the Luciferase Gene:

Method: In brief, the MT-1 cells were grown and maintained in RPMI media containing penicillin and streptomycin with 10% fetal bovine serum at 37 degrees celcius. The MT-1 cells were then transfected with pCl-neo mammalian expression vector (Promega) using the Transfectam Reagent (Promega) transfection kit. Positive colonies were selected by adding 1000 ug/ml G418 antibiotic (Promega) to the tissue culture media. Cell colonies with luciferase activity were identified using the Xenogen IVIS system (Alameda, Calif.). Individual cells were then isolated from high photon emitting colonies and plated. The cells were then grown to subconfluence in RPMI media with antibiotics and 10% FBS in 1000 ug/ml of G418 antibiotic to ensure stable transfection.

Spinal Metastases Model and Establishment of a Transfected Human Breast Cancer Cell Line Expressing the Luciferase Gene:

Results: Of the initial 10 animals injected with MT-1 cells 7 of the 10 animals developed metastatic disease. The mean survival of the animals with tumors was 25 days. Four of the animals showed palpable tumors in the femur and tibias as well as the lower mandible. Two animals developed hind leg paralysis secondary to metastatic disease. All animals with tumors became cachexic. The affected animals appeared well until day 18 after which the animals developed rapid weight loss and overt tumors.

Figure 6:
FIG. 6 is a high definition radiographic (Faxitron) lateral view of rat vertebrae and femur at 21 days post left intracardiac tumor injection.
Figure 7:
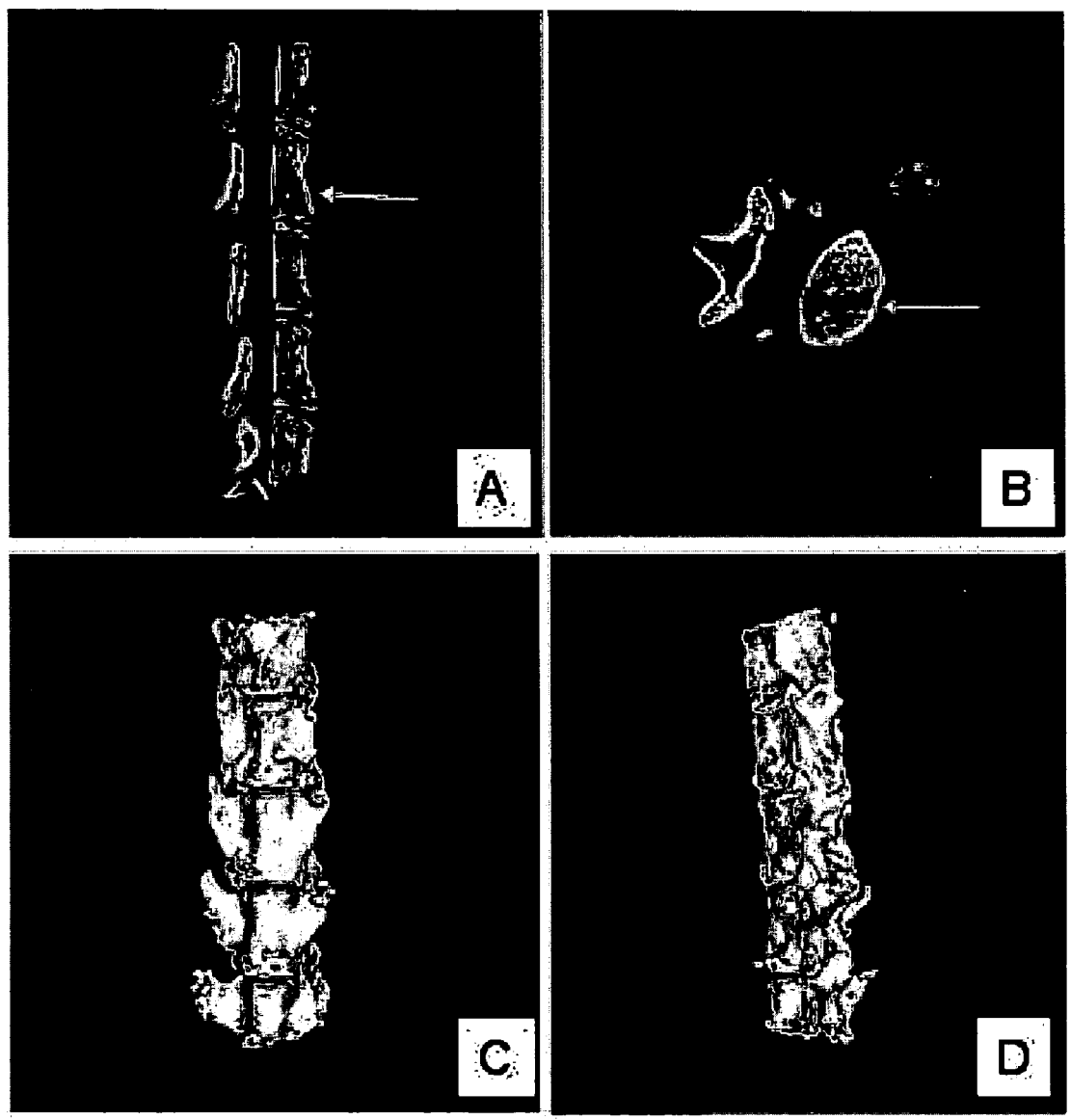
FIG. 7 shows micro-CT analysis of rat vertebrae 21 days following intracardiac injection of MT-1 cells.
Figure 8:
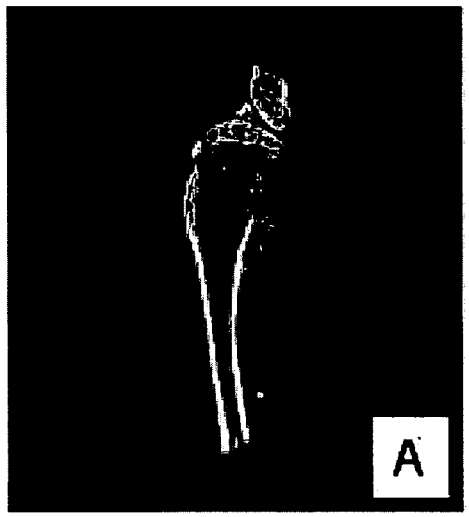
FIG. 8 shows micro-CT analysis of rat tibia 21 days following intracardiac injection of MT-1 cells.
Figure 8:
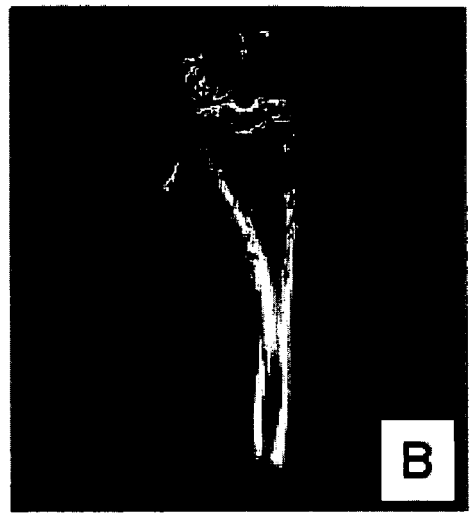
Figure 8:
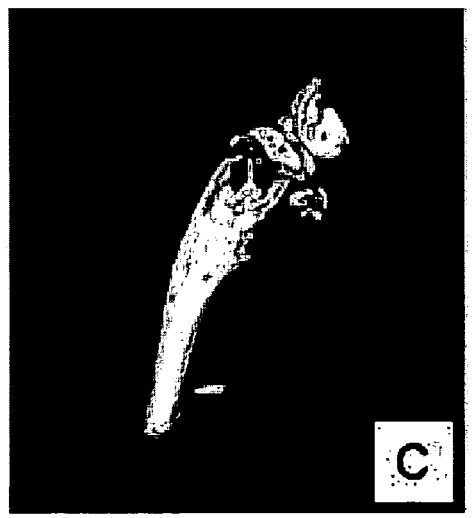
Figure 8:
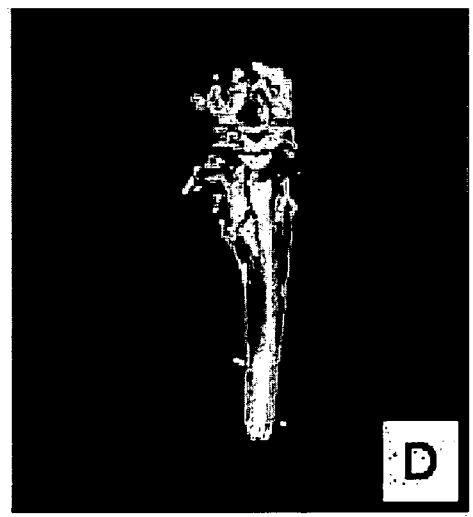

High resolution radiography (Faxitron) indicated lesions within the humerus, femur and tibia as early as day 14 in some animals. For example, FIG. 6 shows a lateral view of rat vertebrae and femur at 21 days post left intracardiac tumor injection. However, lesions could not be detected in the vertebrae of any animals by day 21 by high resolution radiography (Faxitron).

FIGS. 7A-D show micro-CT analysis of rat vertebrae 21 days following intracardiac injection of MT-1 cells. In particular, FIGS. 7A-D show sagittal, transverse, coronal 3D reconstruction and sagittal 3D reconstruction, respectively. Micro-CT analysis of the thoracic and lumbar spines of these animals showed multiple lytic lesions within the vertebrae. Similar lytic lesions were identified in the humerus, tibia and femur.

FIGS. 8A-D show micro-CT analysis of rat tibia 21 days following intracardiac injection of MT-1 cells. In particular, FIGS. 8A-D show sagittal, transverse, coronal 3D reconstruction and sagittal 3D reconstruction, respectively.

The mean area of the lytic lesions within the lumbar vertebrae was 2.92 mm$^2$ and 2.14 mm$^2$ in the thoracic vertebrae. The lesions approximated ⅓ of the vertebral body size in both the lumbar and thoracic vertebrae imaged, as summarized in TABLE 2.

TABLE 2

Vertebral Body Size and Tumor Size (microCT)

| | Vertebral Body | | Osteolytic Lesion (Tumor) | |
|---|---|---|---|---|
| | Sagittal (mm$^2$) | Coronal (mm$^2$) | Sagittal (mm$^2$) | Coronal (mm$^2$) |
| Lumbar (n = 3) | 9.4 | 7.09 | 2.92 | 2.3 |
| Thoracic (n = 3) | 6.64 | 6.89 | 2.14 | 1.69 |

Histological analysis of the vertebrae confirmed the presence of osteolytic tumor within the long bones and vertebrae of the affected animals. Of the twenty animals inoculated with MT-1/luc+ cells similar results were found. All animals showed localization of bioluminescent signal to the spine or long bones by day 21. However, the bioluminescent signal intensity was quite variable. Nine of the twenty animals had either gross visible tumors or cachexia. Bioluminescent imaging of these animals showed a similar pattern of metastases among these animals. A high signal was obtained from the lumbar and thoracic spine, the humerus, femur and tibia in addition to the lung. Micro-CT scans of these animals indicated gross lytic lesions within the vertebral bodies and long bones. Subsequent histological staining with H&E, keratin and immunohistochemical staining for human EGF-r confirmed the presence of human breast cancer cells within the aforementioned sites.

Figure 9:
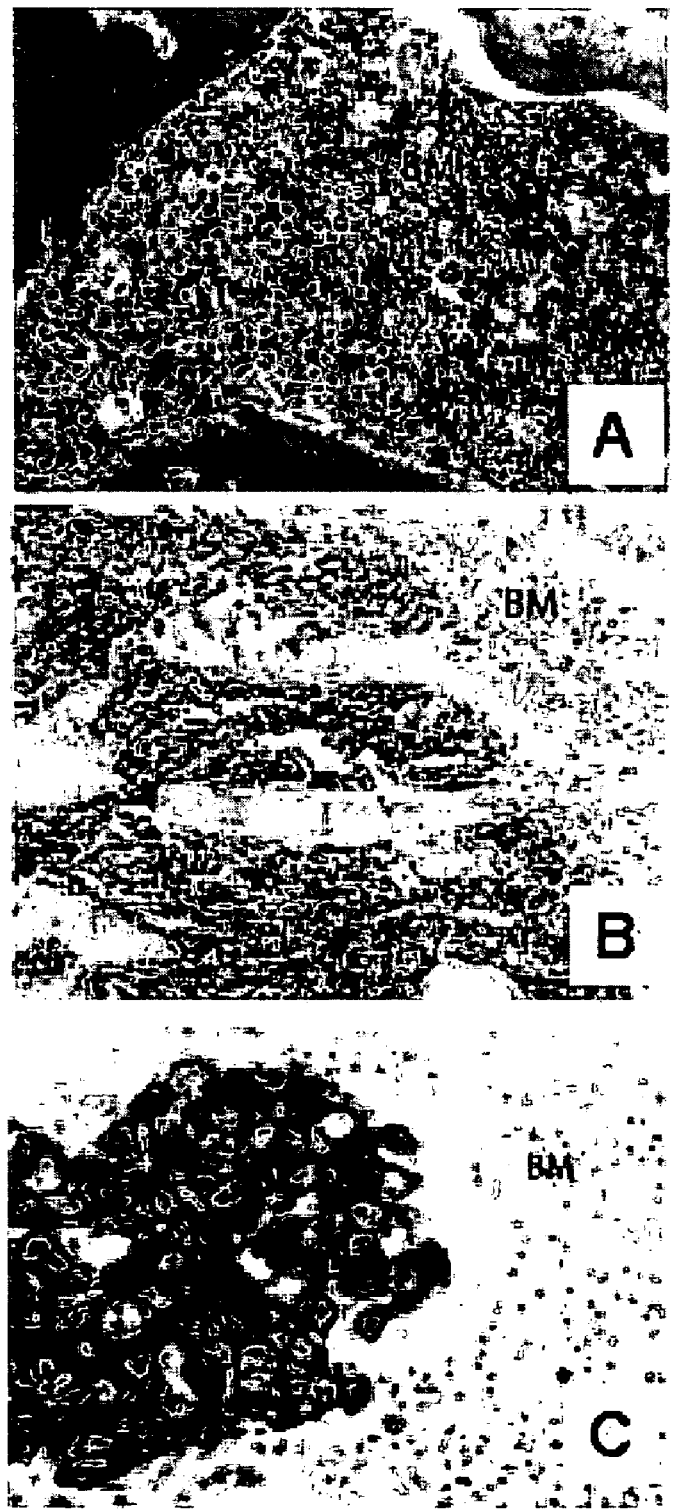
FIG. 9 shows histological and immunohistochemical staining of MT-1 cells within vertebrae.

FIGS. 9A-C show histochemical and immunohistochemical staining of MT-1 cells within vertebrae. In particular, FIGS. 9A-C show H&E staining (10×); Keratin staining (brown) indicating tumor invasion of the bone and bone marrow (5×); and Human EGF-r immunohistochemistry (brown) of MT-1 cells within a vertebrae (20×), respectively. "T" indicates tumor, while "BM" indicates bone marrow. Four of the animals had the highest signals within the chest cavity and gross dissection revealed large metastatic tumors within the lung. Six animals showed a diffuse weak bioluminescent signal localized to the thoracic and lumbar spine. Histological confirmation of tumors within the spine was verified in only two of these animals with one animal having metastases identified in the spinal cord. One animal died a few hours following intracardiac tumor injection.

Determination of the Effect of PDT in Vertebrae and Long Bones with Metastases:

Method: Thirty mu/mu nude rats were used in this part of the study. The rats received a left ventricular intracardiac injection with MT-1 cells as described earlier. At day 21 post injection each animal was anesthetized with 2% halothane/air mixture and placed on a custom made radiolucent stereotactic jig in the left lateral decubitus position. Prior to this it was established by histological methods that animals with tumors contained tumor in most vertebral bodies and long bones. Because lesions within the vertebral bodies could not be detected by fine detail radiography, T12 and L4 vertebrae were selected as representative levels for treatment. An 18 g needle was placed on the cortex of the targeted vertebrae or long bone with the use of a mini C-arm image intensifier. A 300 mW diode laser coupled to a 200 um fiber was used to deliver 690 nm light. BPD-MA was administered intravenously at a dose of 2 mg/kg prior to the administration of the light dose. Drug light intervals included 1 hour, 3 hours and 24 hours. Light doses ranged from 25 J to 150 J. Light was delivered at 150 mW for all treatments and the effects of different drug light intervals and different light doses using a fixed drug concentration were evaluated. The animals were examined for paralysis post treatment. The animals were sacrificed using $CO_2$ inhalation. Vertebrae were then harvested and fixed in 10% formalin for 7 days. Micro-CT images were obtained and then the samples were decalcified in 10% formic acid for 7 days. The tissue was then blocked and paraffin embedded and 10 um sections were cut. The sections were analyzed under light microscopy using H&E staining as well as TUNEL and human EGF-r immunohistochemistry. The area of effect as denoted by necrosis and apoptosis was identified and measured using a Nikon slide scanner and Image Pro software.

Targeted Lesions:

Method: Twenty nude mu/mu (Harlan) female rats (4-6 weeks of age) were used in this part of the study. The protocol was in accordance with the Canadian Council on Animal Care prior to initiation. Prior to injection each animal was anesthetized with 2% halothane/air mixture in a sterile environment. Twenty animals were used for injection. The chest was prepared with alcohol and 2×10$^6$ MT-1luc+ cells, a human breast cancer cell line carrying the luciferase reporter gene, were injected into the left ventricle using a 1 ml syringe with a 26 g needle. Pulsatile blood in the syringe was ensured prior to each injection. The animals were placed back into their cages and fed water and rat chow ad libitum. At day 18 the animals were imaged using the Xenogen IVIS system. To do this 100 mg/kg luciferin was injected into the peritoneal cavity of each animal and each animal was imaged 5 minutes following injection for a 1 to 5 minute image acquisition period. The animals were then imaged on the same custom made stereotactic radiolucent jig using a mini-C-arm image intensifier which allowed correlation of the bioluminescent signal to the vertebrae. FIGS. 1A-C show stereotactic targeting of bioluminescent metastatic lesions using a mini-C-arm image intensifier. FIG. 1A is a bioluminescent overlay image of a nude rat with metastatic lesions on a radio lucent stereotactic jig. FIG. 1B is a fluoroscan image of markers placed along the grid of the stereotactic jig in correlation to the bioluminescent metastases and resulting in localization of the lesion. FIG. 1C shows placement of the fiber optic cable sheath (needle cannula) adjacent to the targeted lesion.

The lesions were then targeted and treated with 25 J or 150 J at a 3 hour drug light interval. The animals were then re-imaged with the Xenogen IVIS system 48 hours post treatment in the stereotactic frame. Signal intensity (photons/second/$cm^2$) at the targeted site before treatment was compared to signal intensity following treatment and compared to lesions not treated using Igor Pro software (Alameda, Calif.). The animals were then sacrificed using $CO_2$ inhalation and the spines and long bones were harvested. Samples were placed in 10% formalin for 7 days and micro-CT images of the vertebrae and long bones were obtained. The vertebrae were examined histologically using H&E staining and immunohistologically with human EGF-r and TUNEL stains as described earlier. ANOVA Bonferroni and two-tailed paired T-test statistical techniques were applied.

Determination of the Effect of PDT in Vertebrae with Metastases:

Results: As summarized in TABLE 3, of the thirty animals injected, twenty-five were analyzed. As summarized in TABLE 4, light doses ranging from 25 J to 150 J had an ablative effect on both normal bone marrow and tumor tissue. The region of effect ranged from 2.5 mm to 22 mm in the rostral-caudal dimension.

TABLE 3

Treatment Groups

| | n = | Death Following Tumor Injection | Death Following Verteporfin Injection | Anesthetic Overdose During Imaging/PDT | Death During PDT |
|---|---|---|---|---|---|
| MT-1 | 20 | 1 | 1 | 1 | 0 |
| MT-1luc+ | 30 | 1 | 2 | 1 | 1 |

TABLE 4

Effect of Different Light Doses on Vertbrae with Metastases

| | 25 J* | 50 J* | 75 J* | 75 J** | 100 J* | 150 J* |
|---|---|---|---|---|---|---|
| Area ($mm^2$) | 8.435 | 15.04 | 52.38 | 82.47 | 45.49 | 80.53 |
| Rostral-Caudal (mm) | 4.59 | 5.66 | 11.67 | 17.47 | 13.8 | 13.05 |
| Antero-Posterior (mm) | 2.62 | 3.89 | 5.09 | 5.05 | 5.05 | 5.78 |

*Treatment given at drug-light interval of 3 hrs
**Treatment given at drug-light interval of 0.75 hrs The effect varied in direct proportion to the amount of light given with the greatest effect being seen with 150 J. However, a 75 J light dose administered at a 1 hour drug light interval produced a similar effect (Table 5).

Figure 14:
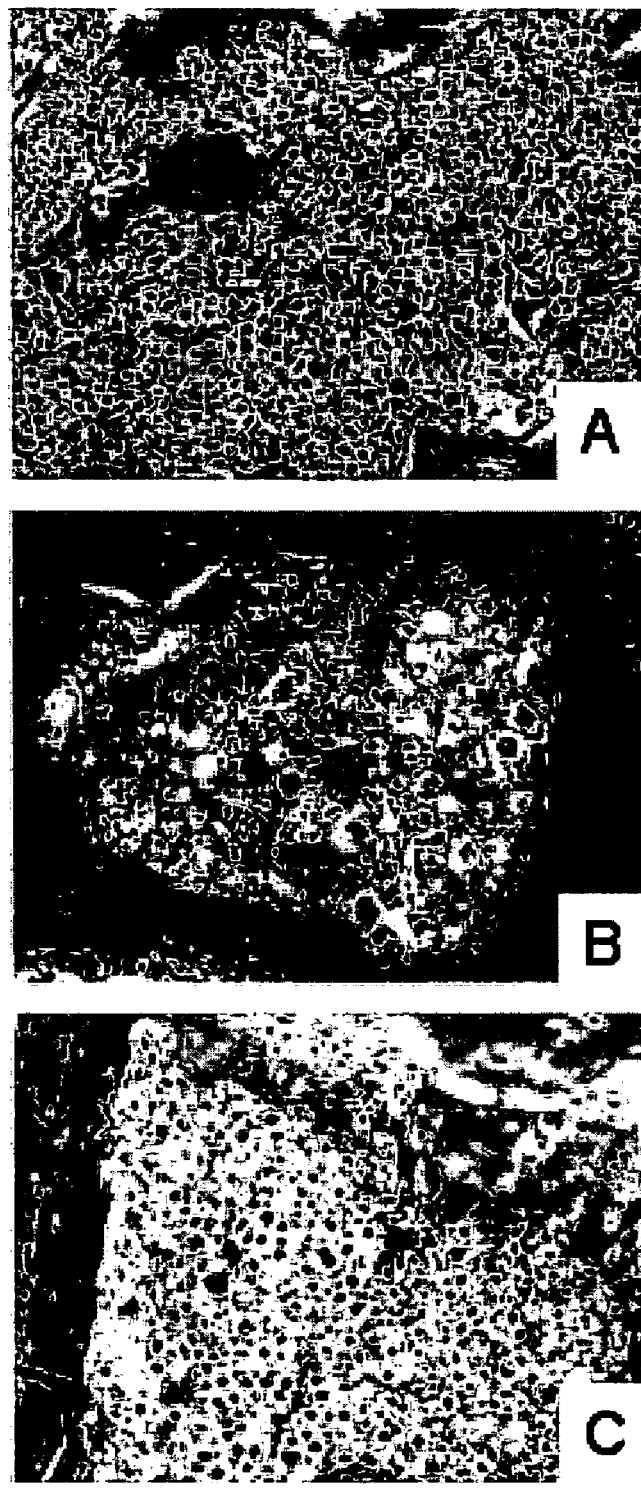
FIG. 14 shows brightfield microscopy of H&E sections containing tumor following PDT treatment.
Figure 15:
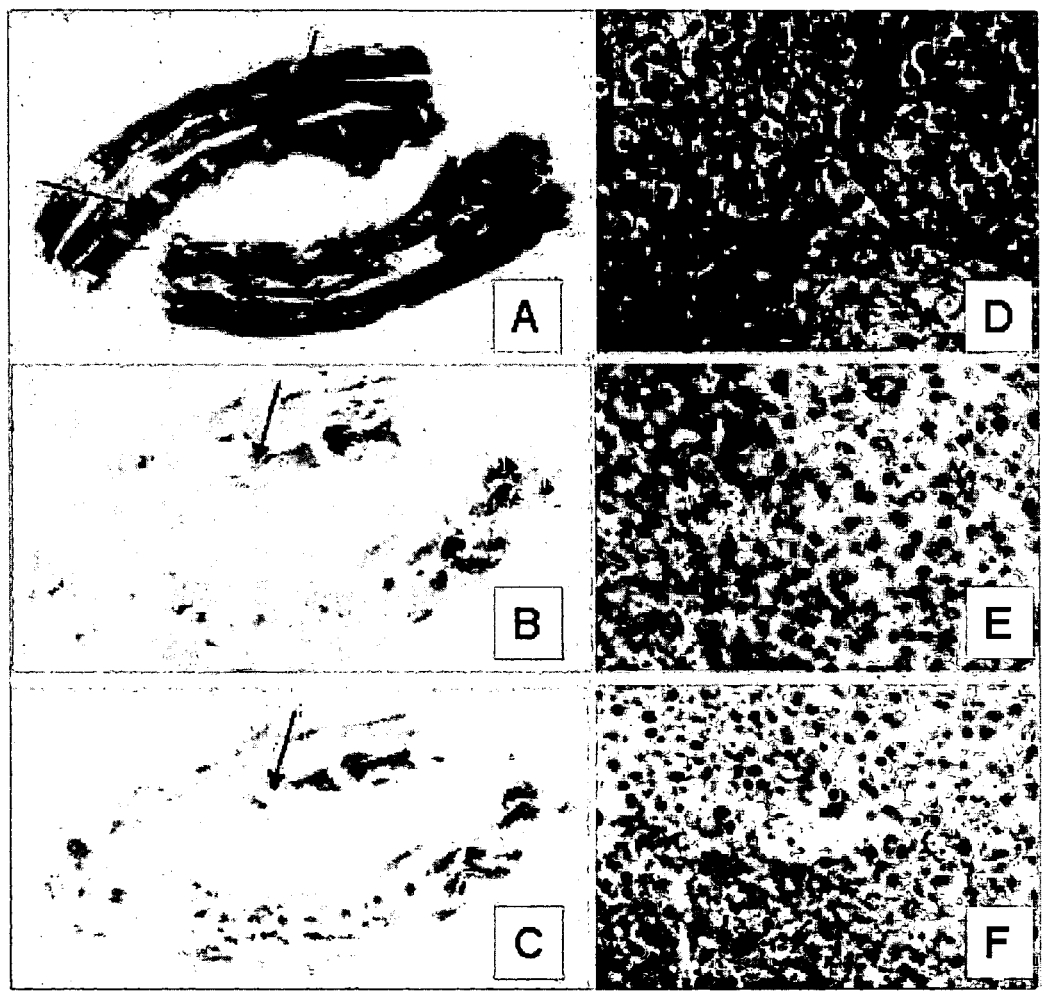
FIG. 15 shows brightfield microscopy of rat vertebrae following PDT treatment.

FIGS. 14A-C show brightfield microscopy of H&E sections containing tumor following PDT treatment. In particular, FIG. 14A shows untreated tumor tissue (10×); and FIGS. 14B-C show treated tumor tissue within a vertebral body at 0× and 20× magnification, respectively. FIGS. 15A-F show brightfield microscopy of rat vertebrae following PDT treatment. FIG. 15A shows an H&E section of section of rat spine (the arrows delineate the diameter of the rostral caudal dimension of the area of effect and demonstrate the position of the high powered images in the right column relative to each other. FIG. 15B shows human EGF-r immunohistochemistry of a contiguous section (2.5×). FIG. 15C shows TUNEL staining of a contiguous section (2.5×). FIG. 15D shows H&E of the same section as in FIG. 15A, but 10× indicating the boundary of affected and unaffected tumor tissue. FIG. 15E shows EGF-r immunohistochemistry at the same site as in D) but on a contiguous section (10×). FIG. 15F shows TUNEL staining at the same site as in FIGS. 15D and E but on a contiguous section (10×). Histological analysis with H&E of the tissue indicated ablation of the tumor tissue. TUNEL staining of the treated tissue was positive at the periphery of the treatment area while necrosis was predominant centrally.

Figure 10:
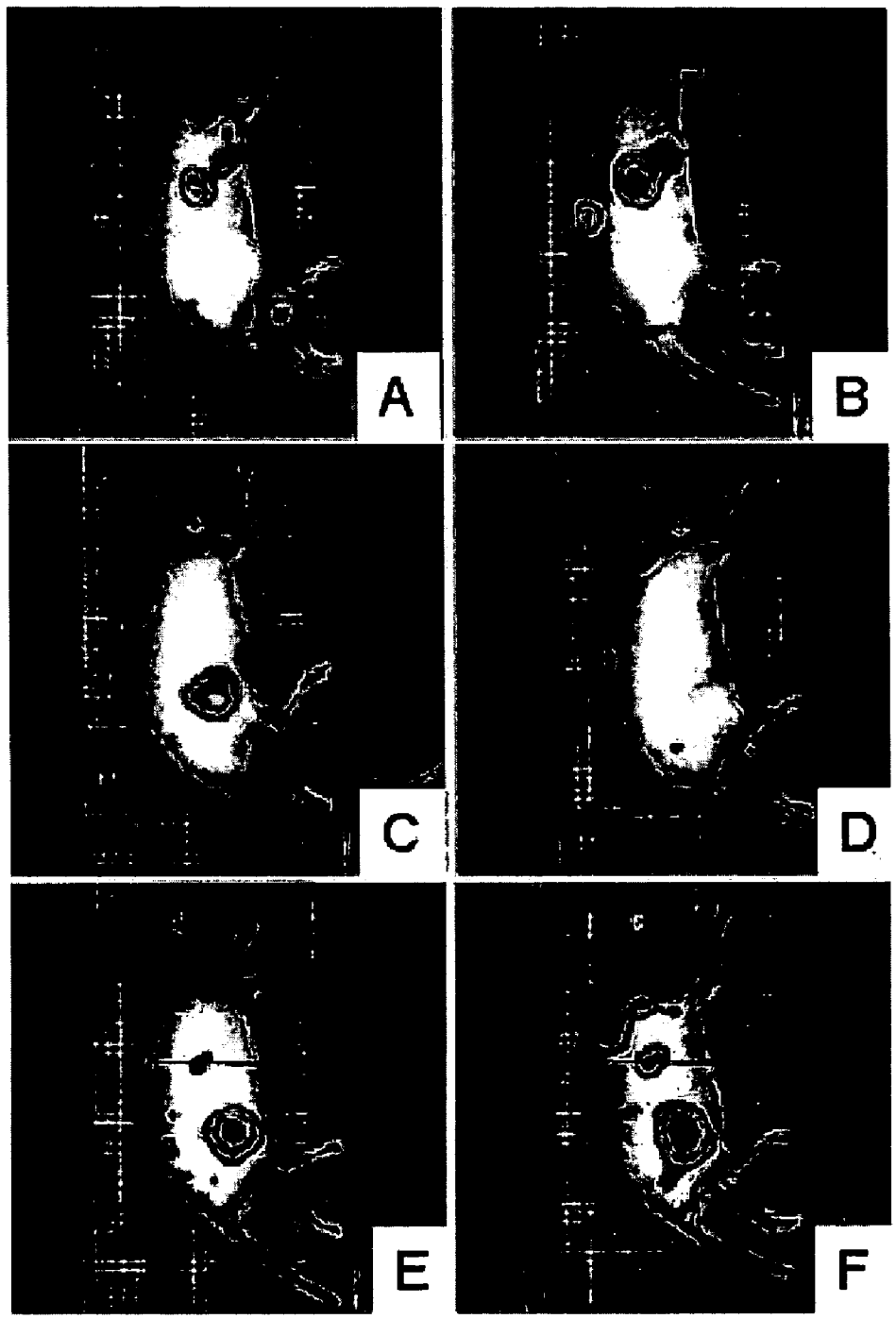
FIGS. 10 and 12 show pre and post-PDT treatment bioluminescent imaging of MT-1luc+ metastatic lesions in mu/mu rats with BPD-MA.

The use of a custom made stereotactic radiolucent jig facilitated localization and targeted treatment of bioluminescent metastases. FIGS. 10A-F and 12A-D show pre and post-PDT treatment bioluminescent imaging of MT-1luc+ metastatic lesions in mu/mu rats with BPD-MA. FIGS. 10A,C,E show pre-treatment bioluminescent imaging. FIGS. 10B,D,F show bioluminescent imaging of the animals imaged in the FIGS. 10A,C,E, respectively, 48 hours following PDT treatment with BPD-MA at 150 J with a drug light interval of 3 hours. FIGS. 12C,D show pre-treatment bioluminescent imaging. FIGS. 12A,B show bioluminescent imaging of the animals imaged in FIGS. 12C,D 48 hours following PDT treatment with BPD-MA at 25 J with a drug light interval of 3 hours. As summarized in FIG. 11 and TABLE 5a, targeted lesions treated with 150 J of light with a 3 hour drug light interval reduced the signal from the targeted site by 87% and decreased tumor growth by 99.8% as compared to control lesions emitted 48 hours following treatment.

TABLE 5A

Bioluminescent Data

| | Mean Count Rx Area | Mean Count UnRx Area | P = |
|---|---|---|---|
| Pre-PDT | $1.02 \times 10^4$ | $1.98 \times 10^3$ | <0.01 |
| Post-PDT | $1.42 \times 10^3$ | $1.65 \times 10^5$ | <0.01 |
| PostRx/PreRx | 0.139 | 83.3 | |

* for drug light interval of 3 hrs 150 J (n = 5)

Figure 11:
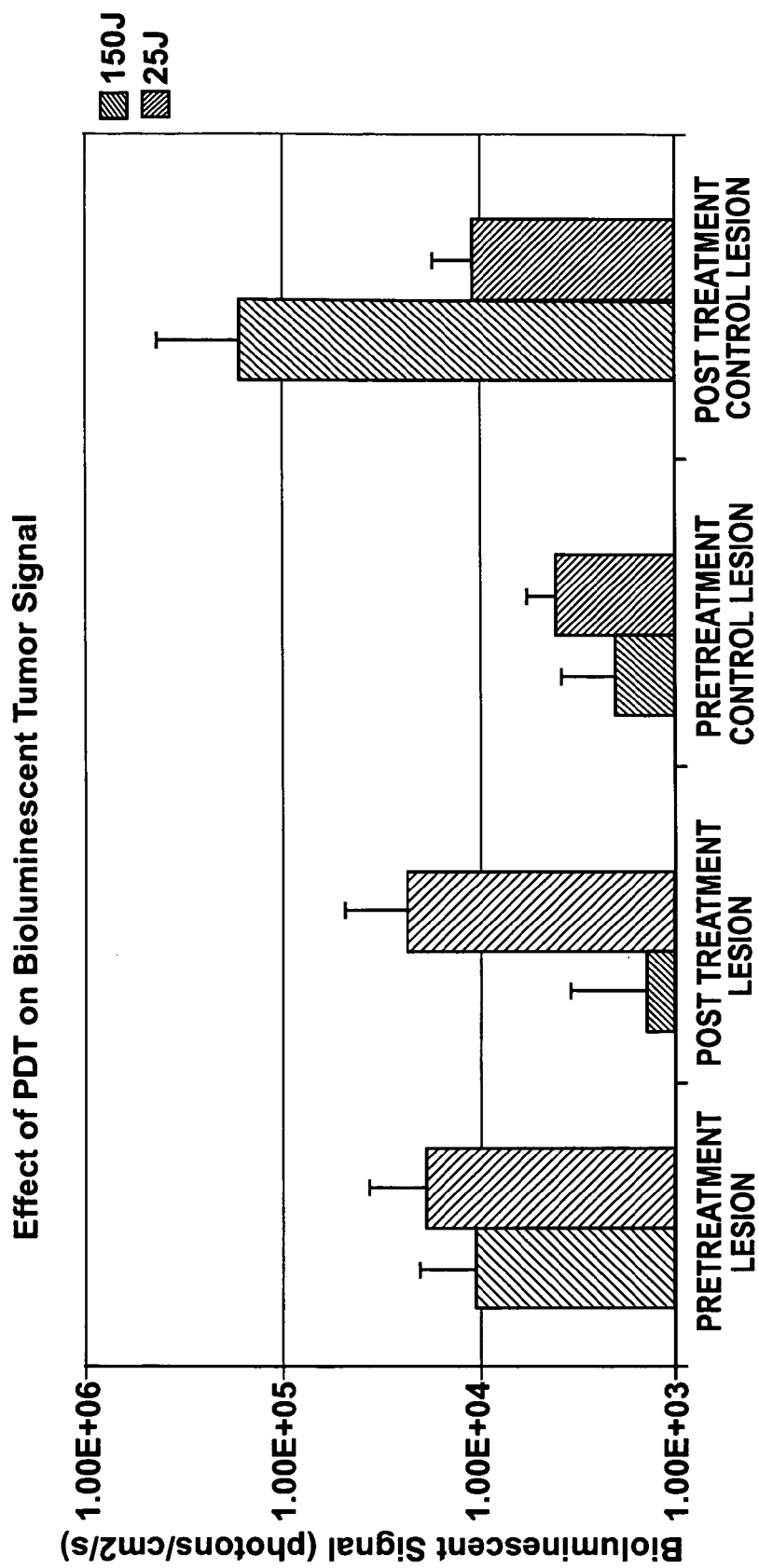
FIG. 11 is a bar graph of the effect of PDT on bioluminescent tumor in rats.
Figure 12:
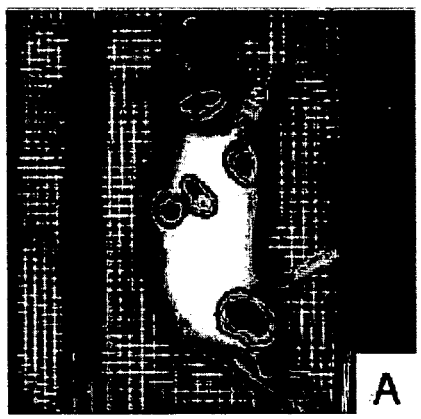
Figure 12:
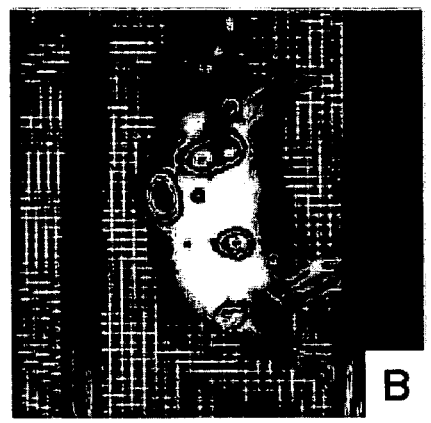
Figure 12:
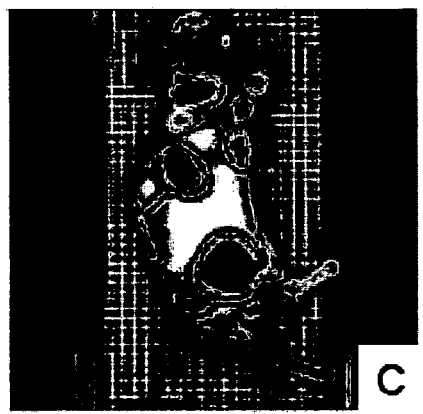
Figure 12:
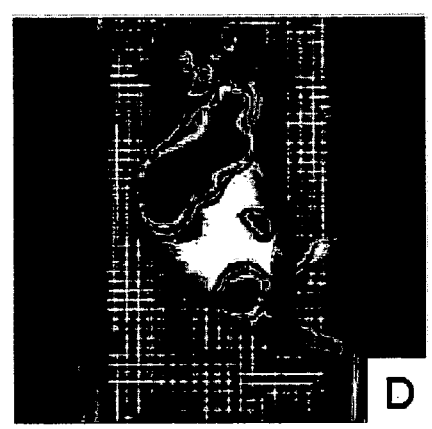

As summarized in FIG. 11 and TABLE 5b, targeted lesions treated with 25 J of light with a 3 hour drug light interval showed a decrease in tumor growth of 66% compared to that of the control lesions.

TABLE 5B

Bioluminescent Data

| | Mean Count Rx Area | Mean Count UnRx Area | P = |
|---|---|---|---|
| Pre-PDT | $1.86 \times 10^4$ | $4.05 \times 10^3$ | <0.05 |
| Post-PDT | $2.33 \times 10^4$ | $1.5 \times 10^4$ | <0.05 |
| PostRx/PreRx | 1.25 | 3.7 | |

* for drug-light interval of 3 hrs 25 J (n = 2)

No effect was seen when light was administered at a 24 hour drug light interval in control animals when light alone or drug alone was administered. As summarized in TABLE 6, hind leg paralysis was seen in animals when treated the 3 hour drug light interval at T12 at light doses between 50 J and 150 J but not at 25 J. No paralysis was seen at the twenty four hour drug light time interval in animals treated with 150 J at T12. No paralysis was seen in animals treated with 150 J at the L5 level of the spine. No paralysis was seen in hind legs of rats following treatment with 150 J directed at the distal femur.

TABLE 6

Effect of Light Dose on the Rat Spinal Cord, Spinal Nerves and Peripheral Nerves

| Light Energy (J) | Vertebral Level Treated | Drug Light Interval (hr) | Hind Leg Paralysis | N = |
|---|---|---|---|---|
| 25 | T12 | 3 | 0 | 5 |
| 50 | T12 | 3 | 2 unilateral | 5 |
| 75 | T12 | 3 | 1 bilateral | 4 |
| 100 | T12 | 3 | 2 unilateral | 3 |
| 125 | T12 | 3 | 1 bilateral | 2 |
| 150 | T12 | 3 | 3 bilateral | 4 |
| 150 | T12 | 0.25 | 4 | 4 |
| 150 | T12 | 24 | 0 | 5 |
| 150 | L4 | 3 | 0 | 5 |
| 150 | Distal Femur | 3 | 0 | 3 |
| Control* | T12 | 3 | 0 | 3 |

*Control - 150 J light delivered without drug.

Referring now to FIGS. 16-19, shown therein, in accordance with the invention, is an exemplary embodiment of a device 10 for enabling light-based therapy for a treatment area of a mammal. In at least one embodiment, the device 10 may be used to facilitate PDT. The device 10 is shown unassembled in FIG. 16. The device 10 comprises an insertion member 12, a locking member 14 and a gripping means 16. The insertion member 12 has a first shaft 18 having a first bore 20 through at least a portion thereof with a first diameter sized for receiving a light conduit (not shown). The insertion member 12 also includes a first head portion 22 near the proximal end of the first shaft 18. The first head portion 22 includes a second bore 24 extending therethrough. The second bore 24 has a second diameter that is larger than the first diameter of the first bore 22. The second bore 22 of the head 24 ends at a land. In one exemplary case, the first bore may have a 2.49 mm diameter.

In one embodiment of the invention, the insertion member 12 further includes external threads 26 on at least a portion of the first shaft 18. In this example, the external threads 26 cover the entire shaft but this is not necessary. In another embodiment, the external threads 26 may not be used; rather another means may be used to secure the insertion member 12 into bone such as longitudinal ribs and the like. In the event that external threads 26 are used and the insertion member 12 is being inserted into bone, then the external threads 26 preferably have low torque and high holding. This is important since the insertion member 12 may need to be secured into bones that may be weak. Therefore, the external threads 26 of the shaft 18 may also have a fine thread. The external threads 26 may comprise a single thread and the thread(s) need not necessarily be continuous.

In an embodiment of the invention, the distal end of the first shaft 18 may have a frusto-conical tip 28 which facilitates inserting the insertion member 12 into hard substances such as bone. However, the frusto-conical tip 28 is not mandatory.

Although FIG. 18 shows the first bore 20 extending throughout the entire length of the insertion member 12. The inventors have found that in some cases it may be preferable to have the light conduit extend a bit past the distal tip of the insertion member as shown in FIG. 20. This is so that the tip of the light conduit can extend into the treatment region for better treatment. The inventors have also found that it is preferable to have shafts that are shorter for the insertion member 12 since it may be difficult to insert the tip of the insertion member 12 into the treatment area. In this case, the light conduit may be extended into the treatment area as mentioned.

The locking member 14 is releasably connectable to the insertion member 12. In one embodiment, the locking member 14 includes a second shaft 30 having a third bore 32 therethrough with a third diameter. The third diameter is less than the second diameter but is sized for receiving the light conduit. The torque to remove the locking member 14 is less than the torque to remove the insertion member 12.

In one embodiment, the second bore 24 of the head portion 22 of the insertion member 12 includes internal threads (not shown) and the second shaft 30 of the locking member 14 includes corresponding external threads 34 on at least a portion of the second shaft 30 for releasably engaging the head portion 22 of the insertion member 12.

The locking member 14 also includes a second head portion 36 with a fourth bore 38. The head portion 36 may be shaped to accommodate use with a drill for inserting the locking member 14 into the insertion member 12. Accordingly, the fourth bore 38 may be sized a bit larger than the third bore 32 in the shaft 30.

In use, the gripping means 16 is disposed within the second bore 24 of the insertion member 12 for holding the optical conduit in place when the locking member 14 is connected to the insertion member 12. In one embodiment, the gripping means 16 may be a flexible gasket seal such as an O-ring. The gripping means 16 also includes a bore for allowing the optical conduit to pass therethrough. The gripping means 16 is able to freely pass inside the threads of the second bore 24 of the head 22 of the insertion member 12.

Referring now to FIG. 20, shown therein an isometric view of the device 10 being assembled. An optical conduit 40, such as an optical fiber for example, is threaded through the locking member 14, the gripping means 16 and finally the insertion member 12. The tip of the optical conduit 40 may extend past the tip of the insertion member 12 as shown in FIG. 20. It should be noted that, prior to assembling the device 10, the insertion member 12 is already located in the treatment area which may be bone in this case. To secure the optical conduit 40 in place, the locking member 14 is connected to the insertion member 12 with the gripping means 16 disposed therebetween. As the locking member 14 is put into place, it pushes the gripping means to the land in the head 22 of the insertion member 12 which leads to the application of a compressive force to the gripping means 16. This causes the gripping means 16 to deform radially inward and apply a constrictive force on the optical conduit 40. Care is taken to ensure that the constrictive force is sufficient to hold the optical conduit 40 in place but not strong enough to damage the optical conduit 40.

The device 10 may be used in the treatment of cancer in bone. The device 10 may also be used in all instances in which PDT treatment is used such as in the PDT treatment of osteomyelitis (SA bacterial) infection of bone. Accordingly, the device may be used in the PDT treatment of non-cancerous lesions in bone.

Referring now to FIG. 21, in another alternative embodiment of the device, the gripping means 16 may include a portion of the locking member 14 and a portion of the insertion member 12. For instance, the head member 24' of the insertion member 12 may include a bore 24' with tapered ends 42 and the gripping member 14 may have a shaft 34' with several teeth or flaps 44. In this case, there is no need for a flexible seal member 16 since the flaps 44 flex inwards when the locking member 14 is connected or inserted into the insertion member 12. The flexing of the flaps 44 provides a constrictive force to hold the optical conduit 40 in place.

In one embodiment of the invention, the device 10 may be a cannulated bone screw assembly. In particular, the insertion member 12 may be a cannulated bone screw, the locking member 14 may be a cannulated locking screw and the gripping means 16 may be a flexible, elastometric O-ring.

In Vivo Studies in Pig Model

Operative Approach:

In this study, 50 kg pigs were used. The pigs were pre-anesthetized with ketamine/xylazine 20/2 mg/Kg IM for induction. An IV line was established and 0.9% saline solution was run at 5 ml/Kg/hr. Verteporfin was administered through the IV line using an infusion pump. The pigs were intubated and maintained on a ventilator with isofluorane/nitrous oxide inhalant by animal care professionals. The pigs were placed prone on a radiolucent surgical table with appropriate bolsters for support and padding. A sterile prep was made with betadine soap and scrub and prep solution. A small stab incision was made over the lumbothoracic spine of the pig.

Figure 22:
FIG. 22 shows an inserted guide pin and the insertion of another guide pin with a cannulated drill.

As shown in FIG. 22, using a cannulated drill, a customized guide pin was inserted through the incision onto the bone. Placement into the vertebral body through a transpedicular and parapedicular approach was facilitated by the use of a CT-Carm. The L1 and L2 vertebrae were targeted.

Figure 23:
FIG. 23 shows an inserted cannulated exchange sheath and the insertion of a cannulated bone screw assembly.
Figure 25:
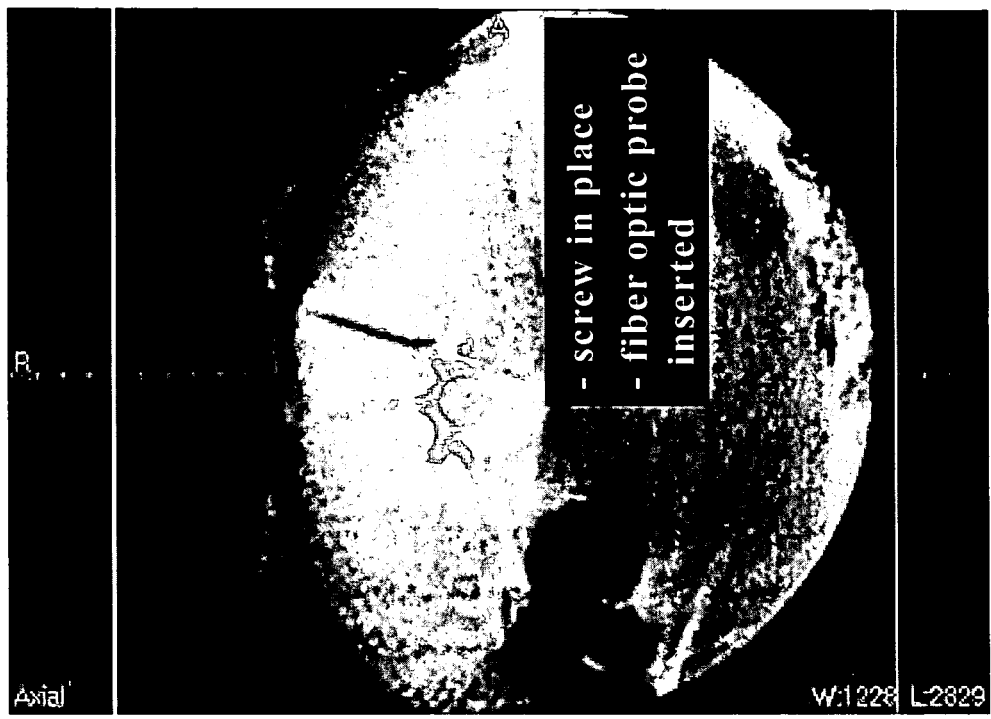
FIGS. 25 and 26 show a vertebrae with a bone screw in place and a fiber optic probe inserted.
Figure 24:
FIG. 24 shows inserted fibre optic cable sheaths and inserted fiber optic cables in a transpedicular placement.
Figure 26:
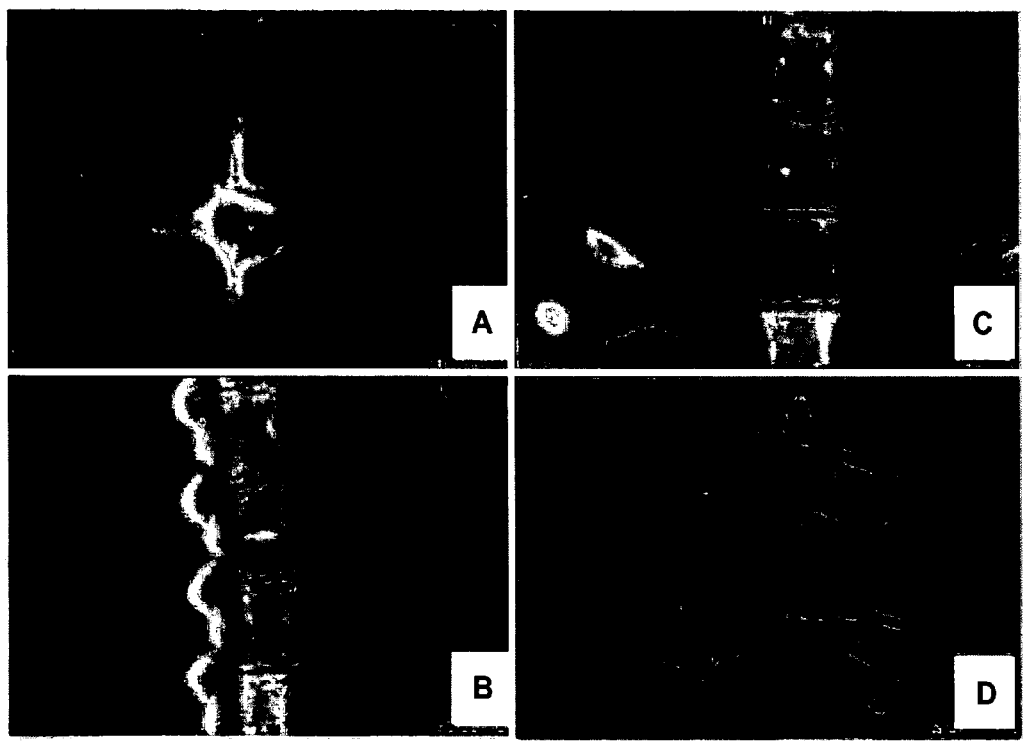

A cannulated exchange sheath was placed over the guide rod and inserted through the incision. The guide rod was then removed, and a fiber optic cable sheath was then inserted down the cannula of the exchange sheath. A cannulated bone screw assembly, which is one exemplary embodiment of a device for facilitating light-based therapy, and in particular photo-dynamic therapy, in accordance with the invention, was then placed around the cannulated exchange sheath and inserted through the incision, as shown in FIG. 23. The cannulated bone screw assembly was pushed down the cannulated exchange sheath. The cannulated bone screw was secured into bone. In this study, the cannulated bone screw was secured into the pedicle of the vertebral body. The cannulated exchange sheath was then removed, leaving the cannulated bone screw assembly and fiber optic cable sheath behind. The cannulated locking screw was tightened into the head of the bone screw, thus compressing the O-ring and locking the fiber optic cable sheath in place. A fiber optic cable was passed down the fiber optic cable sheath, as shown in FIG. 24. FIGS. 25 and 26 show a vertebrae with a bone screw in place and a fiber optic probe inserted.

Detector and diffusing fibers were placed in the same transverse plane. The diffusing fiber was moved incrementally with respect to the detector fiber and differences in power were measured at five different distances from the detector source using a computer aided photomultiplier tube.

A 690 nm light was delivered into the vertebrae at L1 at light doses ranging from 25 J-100 J of energy (four animals received one dose of either 25 J, 50 J, 75 J or 100 J and one control animal received no energy). The light dose took into account the optical properties of the $1^{st}$ and $2^{nd}$ lumbar vertebrae, such that the does refers to the dose at the site of the bone tumor.

Hemostasis was maintained with cautery. Hemostasis was obtained prior to closure. Closure of the fascia was done with #1 vicryl followed by 2-0 vicryl for the subcutaneous tissue followed by 2-0 proline suture for skin. A sterile bandage was applied over the incision.

The pigs were extubated and allowed activity as tolerated with diet as tolerated. The pigs were given post-op analgesia (buprenorphine 0.005-0.01 mg/Kg IM or carprofen 0.1-1 mg/Kg IM) as necessary. The pigs were observed for development of hindleg paralysis and sacrificed 24 hours post-op if no paralysis occurred. In the even that paralysis occurred, the animal was sacrificed as necessary.

End Points of Study:

The end points of the study included: a) in vivo attenuation of 690 nm light in vertebrae; b) observation for hindleg paralysis secondary to the treatment; c) the spinal cord was harvested and examined histologically using H&E staining to determine structural damage from the treatment; and d) a sample of vertebral body was harvested and imaged with micro-CT to determine the bone density for each vertebral body in which the light attenuation studies were conducted.

Results:

Five pigs were used in the study. Ten vertebrae were targeted, each vertebrae having two probes placed (one on the right and one on the left side) making for a total of 20 insertions of the customized implantation device.

There was one complication with respect to inserting the guide rod in one vertebra (1/20) leading to post-operative paresis. One pig developed anaphylactic shock and died, one pig developed anaphylactic shock and was resuscitated and survived without complications. In the other 3 pigs (6 vertebrae) there were no complications. There were no complications attributed to the PDT, for example, no hindleg paralysis.

Figure 27:
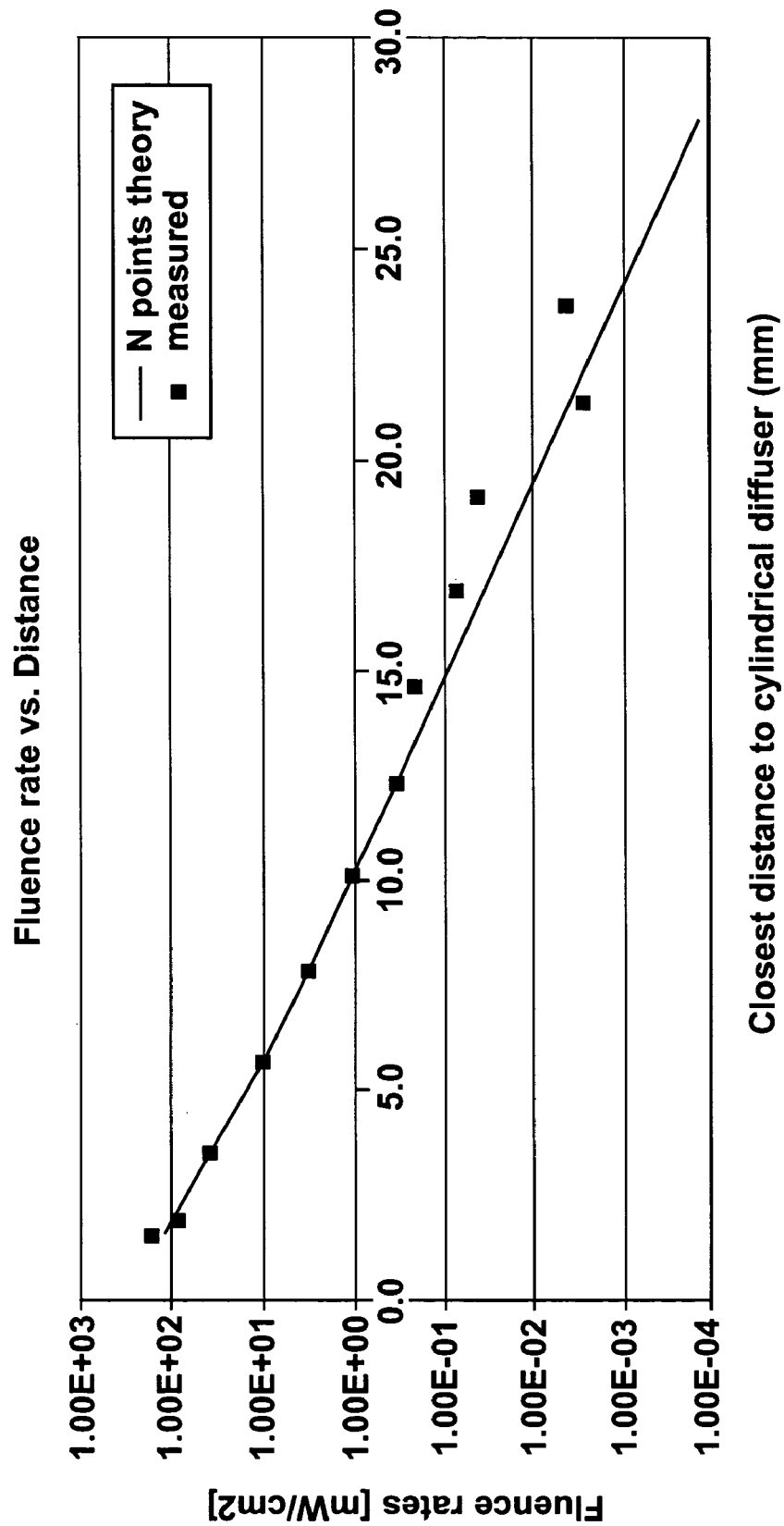
FIGS. 27 and 28 are graphs showing some of the results of the light attenuation studies in bone; and, FIG. 29 shows some of the equipment used in the in vivo pig study.
Figure 28:
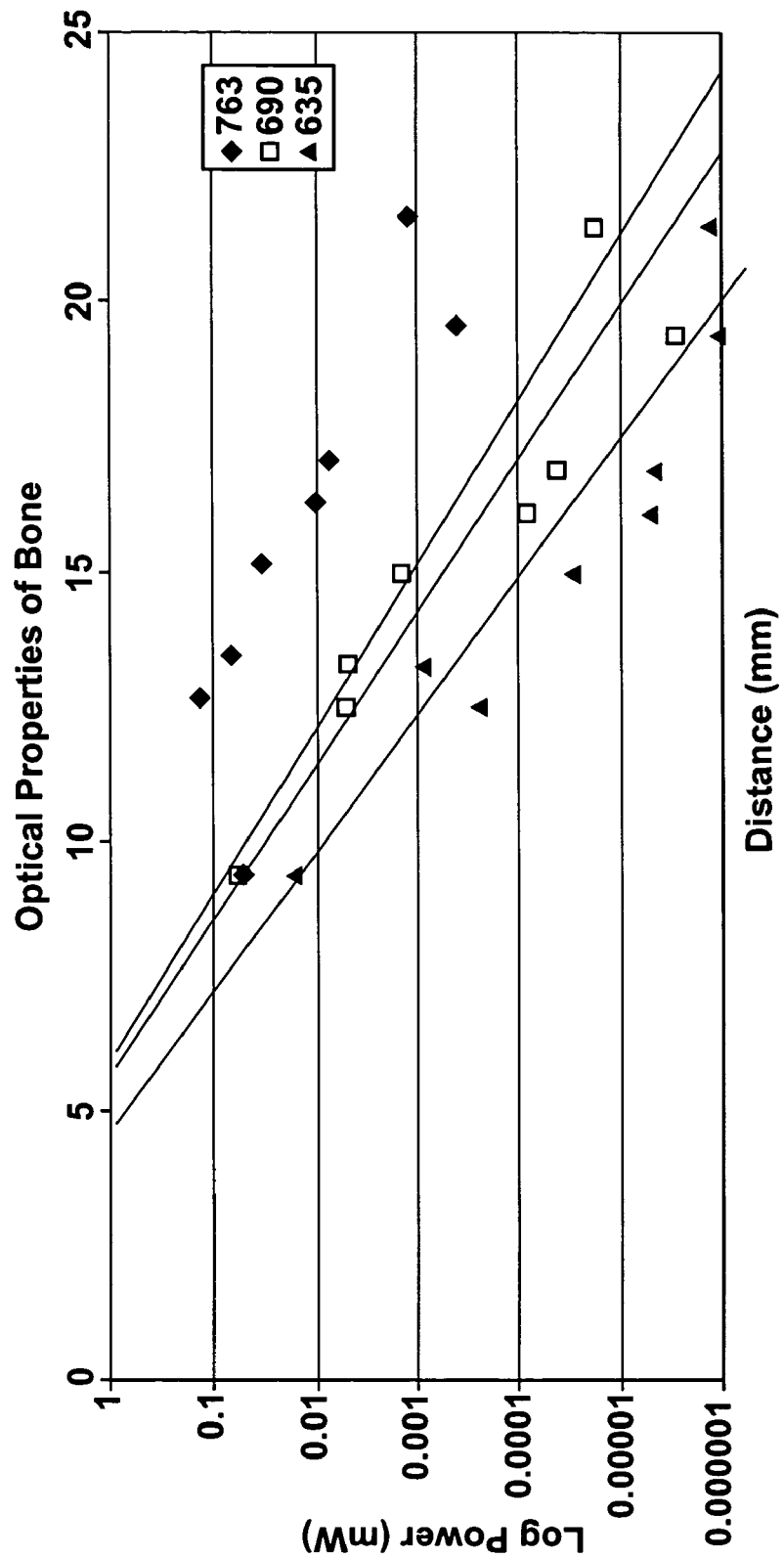

The use of a CT scan intraoperatively allowed the exact distance between the delivery fiber and the detector fiber to be determined. This enabled the determination of the attenuation of light within the vertebrae, as shown in FIGS. 27 and 28. The treatment of the vertebrae with PDT allowed the area of effect of the treatment to be correlated with the light attenuation data, thus allowing a dose response curve for vertebral bone to be determined. It is anticipated that in humans, a light dosage in the range of 150 J/cm will be used.

Pigs were used in this study because the bone density and structure of their vertebrae resembles that of humans. Therefore, pig vertebrae have similar optical properties to humans. In particular, the anatomical dimensions and structure of the porcine vertebrae (thoracic, lumbar inclusive) are similar to that of human. Accordingly, pig vertebrae allow one to test whether PDT could be effective in a large bone with healthy or diseased marrow. The data shows that PDT is capable of producing a volume effect that would be compatible with treating a vertebral bodies in humans.

The cannulated bone screw and the fibre optic cable sheath may remain in the body for repeated treatments with photo-dynamic therapy. This ensures that therapy is provided to the same part of the treatment area across multiple treatments. Once it has been decided not to use PDT treatment at the site of the bone screw anymore, the following method is used. The cannulated locking screw is unlocked and removed from the mammal. The cannulated exchange sheath is reinserted in the mammal around the fiber optic cable sheath. The fiber optic sheath is removed from the mammal. Optionally, the cannulated bone screw is also removed from the mammal. Bone cement is injected through the cannulated exchange sheath, and the cannulated exchange sheath is slowly removed as the bone cement dries.

Figure 29:
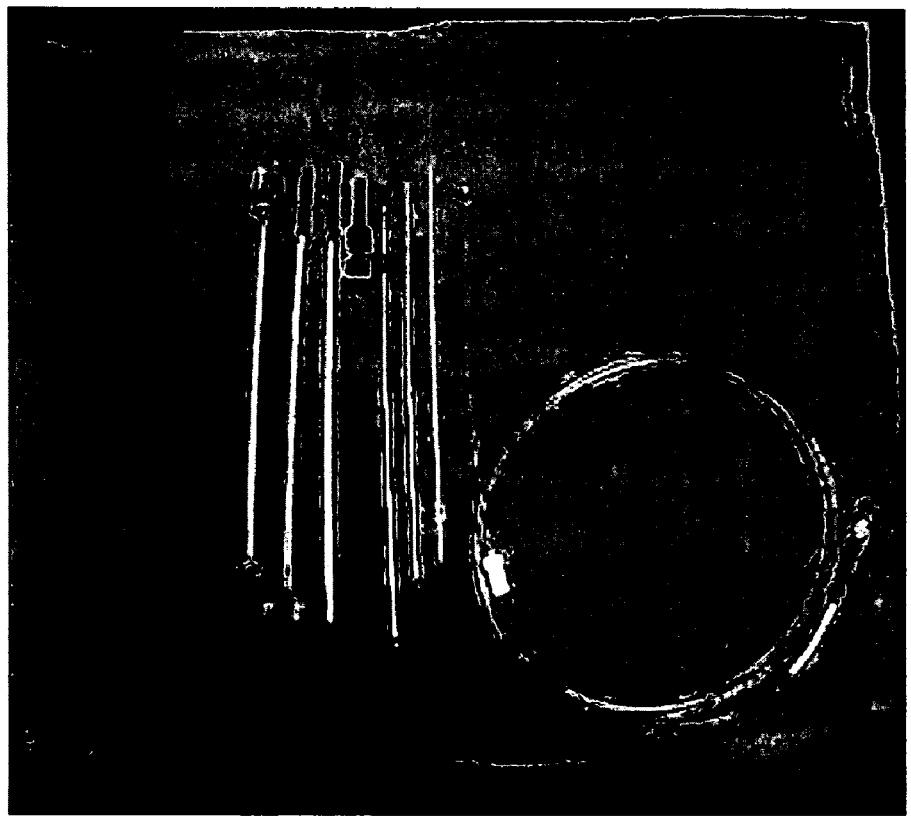

FIG. 29 shows some of the equipment used in the in vivo pig study. At the far right is a fiber optic cable. To the left of the fiber optic cable is a fiber optic cable sheath. To the left of the fiber optic cable sheath is a guide pin. To the left of the guide pin is a cannulated exchange sheath. To the left of the cannulated exchange sheath is a cannulated bone screw assembly.

It should be noted that various embodiments of the device developed herein facilitates the delivery of light energy into a treatment area, in this case bone, as part of a PDT treatment to allow single or repeated treatment regiments. If repeated treatment regiments are used, then advantageously, the various embodiments of the device enable for the repeated delivery of light energy with enough precision to ensure that the delivery of light energy to the treatment site is substantially reproducible with the device.

It should be understood that various modifications can be made to the embodiments described and illustrated herein, without departing from the invention, the scope of which is defined in the appended claims.

REFERENCES

1. Tombolini, V., et al., *Radiation therapy of spinal metastases: results with different fractionations*. Tumori, 1994. 80(5): p. 353-6.
2. Walsh, G. L., et al., *Anterior approaches to the thoracic spine in patients with cancer: indications and results*. Ann Thorac Surg, 1997. 64(6): p. 1611-8.
3. Milker-Zabel, S., et al., *Clinical results of retreatment of vertebral bone metastases by stereotactic conformal radiotherapy and intensity-modulated radiotherapy*. Int J Radiat Oncol Biol Phys, 2003. 55(1): p. 162-7.
4. Katagiri, H., et al., *Clinical results of nonsurgical treatment for spinal metastases*. Int J Radiat Oncol Biol Phys, 1998. 42(5): p. 1127-32.
5. Ryu, S., et al., *Image-guided and intensity modulated radiosurgery for patients with spinal metastasis*. Cancer, 2003. 97(8): p. 2013-8.
6. Fingar, V. H., et al., *Analysis of acute vascular damage after photodynamic therapy using benzoporphyrin derivative (BPD)*. Br J Cancer, 1999. 79(11-12): p. 1702-8.
7. Takeuchi, Y., et al., *Induction of intensive tumor suppression by antiangiogenic photodynamic therapy using polycation-modified lipsomal photosensitizer*. Cancer, 2003. 97(8): p. 2027-34.
8. Rousset, N., et al., *Cellular distribution and phototoxicity of benzoporphyrin derivative and Photofrin*. Res Exp Med (Berl), 2000. 199(6): p. 341-57.
9. Wiedmann, M., et al., *Neoadjuvant photodynamic therapy as a new approach to treating hilar cholangiocarcinoma: a phase II pilot study*. Cancer, 2003. 97(11): p. 2783-90.
10. Sutedja, G. and P. E. Postmus, *The role of photodynamic therapy in the management of stage I/II NSCLC*. Lung Cancer, 2001. 34 Suppl 3: p. S35-8.
11. Hendren, S. K., et al., *Phase II trial of debulking surgery and photodynamic therapy for disseminated intraperitoneal tumors*. Ann Surg Oncol, 2001. 8(1): p. 65-71.
12. Nathan, T. R., et al., *Photodynamic therapy for prostate cancer recurrence after radiotherapy: a phase I study*. J Urol, 2002. 168(4 Pt 1): p. 1427-32.
13. Engebraaten, O. and O. Fodstad, *Site-specific experimental metastasis patterns of two human breast cancer cell lines in nude rats*. Int J Cancer, 1999. 82(2): p. 219-25.
14. Weber, K. L. and M. C. Gebhardt, *What's new in musculoskeletal oncology*. J Bone Joint Surg Am, 2003. 85-A (4): p. 761-7.
15. Faul, C. M. and J. C. Flickinger, *The use of radiation in the management of spinal metastases*. J Neurooncol, 1995. 23(2): p. 149-61.
16. Wedin, R., H. C. Bauer, and L. E. Rutqvist, *Surgical treatment for skeletal breast cancer metastases: a population-based study of 641 patients*. Cancer, 2001. 92(2): p. 257-62.
17. Sundaresan, N., et al., *Treatment of neoplastic spinal cord compression: results of a prospective study*. Neurosurgery, 1991. 29(5): p. 645-50.
18. Rousset, N., et al., *Effects of photodynamic therapy on adhesion molecules and metastasis*. J Photochem Photobiol B, 1999. 52(1-3): p. 65-73.
19. Richter, A. M., et al., *Photosensitizing efficiency of two regioisomers of the benzoporphyrin derivative monoacid ring A (BPD-MA)*. Biochem Pharmacol, 1992. 43(11): p. 2349-58.
20. Richter, A. M., et al., *Photosensitizing potency of structural analogues of benzoporphyrin derivative (BPD) in a mouse tumour model*. Br J Cancer, 1991. 63(1): p. 87-93.
21. Jamieson, C. H., W. N. McDonald, and J. G. Levy, *Preferential uptake of benzoporphyrin derivative by leukimic versus normal cells*. Leuk Res, 1990. 14(3): p. 209-19.
22. Richter, A. M., et al., *Biodistribution of tritiated benzoporphyrin derivative (3H-BPD-MA), a new potent photosensitizer, in normal and tumor-bearing mice*. J Photochem Photobiol B, 1990. 5(2): p. 231-44.
23. Gluck, S., et al., *The selective uptake of benzoporphyrin derivative mono-acid ring A (BPD-MA) in differential cell kill of multiple myeloma cells in vitro*. Photochem Photobiol, 1996, 63(6): p. 846-53.
24. Kurohane, K., et al., *Photodynamic therapy targeted to tumor-induced angiogenic vessels*. Cancer Lett, 2001.167 (1): p. 49-56.
25. Momma, T., et al., *Photodynamic therapy of orthotopic prostate cancer with benzoporphyrin derivative: local control and distant metastasis*. Cancer Res, 1998. 58(23): p. 5425-31.
26. Cincotta, L. et al., *Benzophenothiazine and benzoporphyrin derivative combination phototherapy effectively eradicates large murine sarcomas*. Photochem Photobiol, 1996. 63(2): p. 229-37.
27. Richter, A. M., et al., *Liposomal delivery of a photosensitizer, benzoporphyrin derivative monoacid ring A (BPD), to tumor tissue in a mouse tumor model*. Photochem Photobiol, 1993. 57(6): p. 1000-6.
28. Takeuchi, A., et al., *A new method of bone tissue measurement based upon light scattering*. J Bone Miner Res, 1997. 12(2): p. 261-6.
29. Casas, A., et al., *In vitro photosensitisation of a murine mammary adenocarcinoma cell line with Verteporfin*. Cell Mol Biol (Noisy-le-grand), 2002. 48(8): p. 931-7.
30. Rehemtulla, A., et al., *Rapid and quantitative assessment of cancer treatment response using in vivo bioluminescence imaging*. Neoplasia, 2000. 2(6): p. 491-5.
31. Wetterwald, A., et al., *Optical imaging of cancer metastasis to bone marrow: a mouse model of minimal residual disease*. Am J Pathol, 2002. 160(3): p. 1143-53.

We claim:

1. A device for providing light-based therapy for a treatment area in a bone of a mammal, comprising:
    a) an optical conduit for delivering the light-based therapy;
    b) an insertion member for insertion into the bone of the mammal at or near the treatment area, the insertion member including a first shaft having a first bore through at least a portion thereof, the first bore having a first diameter sized for receiving the optical conduit, the first shaft also having a securing means on at least an external portion thereof for securing the insertion member at or near the treatment area in the bone of the mammal, a head portion near a proximal end of the first shaft having a second bore extending therethrough, the second bore having a second diameter larger than the first diameter;

c) a locking member releasably connectable to the insertion member for holding the optical conduit in place during treatment, the locking member including a second shaft having a third bore therethrough with a third diameter, the third diameter being less than the second diameter but being sized for receiving the optical conduit; and, d) a gripping means disposed within the second bore of the insertion member for holding the optical conduit in place when the locking member is connected to the insertion member.

2. The device of claim 1, wherein the securing means includes external threads on at least a portion of the first shaft.

3. The device of claim 2, wherein the external threads of the first shaft are of low torque and high holding.

4. The device of claim 1, wherein the second bore of the head portion of the insertion member includes internal threads, and the second shaft of the locking member includes corresponding external threads on at least a portion of the second shaft for releasably engaging the head portion of the insertion member.

5. The device of claim 1, wherein a distal end of the first shaft has a frusto-conical tip.

6. The device of claim 1, wherein the gripping means includes a flexible seal.

7. The device of claim 1, wherein the gripping means includes several flaps located near a distal end of the locking member and a tapered portion of the first bore in the first shaft having a taper for applying a compressive inward force to the several flaps to grip the optical conduit when the locking member is inserted within the insertion member.

8. The device of claim 1, wherein the optical conduit includes an optical fiber.

* * * * *